US006359130B1

(12) United States Patent
Singh et al.

(10) Patent No.: US 6,359,130 B1
(45) Date of Patent: *Mar. 19, 2002

(54) BRIDGED INDENOPYRROLOCARBAZOLES

(75) Inventors: Jasbir Singh, Gilbertsville; Robert L. Hudkins, Chester Springs; John P. Mallamo, Glenmoore; Theodore L. Underiner, Malvern; Rabindranath Tripathy, Landenberg, all of PA (US)

(73) Assignee: Cephalon, Inc., West Chester, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/572,160

(22) Filed: May 17, 2000

Related U.S. Application Data

(62) Division of application No. 09/325,140, filed on Jun. 3, 1999, now Pat. No. 6,127,401.
(60) Provisional application No. 60/088,114, filed on Jun. 5, 1998.

(51) Int. Cl.$^7$ .............................................. C07D 498/22
(52) U.S. Cl. ...................... 540/546; 540/468; 540/469; 540/472; 540/479; 540/556; 540/579
(58) Field of Search ................................ 540/546, 468, 540/469, 472, 479, 556, 579

(56) References Cited

U.S. PATENT DOCUMENTS

| | | | |
|---|---|---|---|
| 4,735,939 A | 4/1988 | McCoy et al. | 514/211 |
| 4,816,450 A | 3/1989 | Bell et al. | 514/25 |
| 4,877,776 A | 10/1989 | Murakata et al. | 514/43 |
| 4,923,986 A | 5/1990 | Murakata et al. | 540/545 |
| 5,063,330 A | 11/1991 | Leprince et al. | 315/111.21 |
| 5,461,146 A | 10/1995 | Lewis et al. | 540/545 |
| 5,475,110 A | 12/1995 | Hudkins et al. | 546/256 |
| 5,516,771 A | 5/1996 | Dionne et al. | 514/211 |
| 5,545,636 A | 8/1996 | Heath, Jr. et al. | 514/214 |
| 5,552,396 A | 9/1996 | Heath, Jr. et al. | 514/183 |
| 5,589,365 A | 12/1996 | Kojiri et al. | 435/85 |
| 5,589,472 A | 12/1996 | Vice | 514/183 |
| 5,591,842 A | 1/1997 | Kojiri et al. | 536/27.1 |
| 5,591,855 A | 1/1997 | Hudkins et al. | 546/256 |
| 5,594,009 A | 1/1997 | Hudkins et al. | 514/338 |
| 5,616,724 A | 4/1997 | Hudkins et al. | 548/417 |
| 5,621,098 A | 4/1997 | Heath, Jr. et al. | 540/472 |
| 5,621,100 A | 4/1997 | Lewis et al. | 540/545 |
| 5,621,101 A | 4/1997 | Lewis et al. | 540/545 |
| 5,624,949 A | 4/1997 | Heath, Jr. et al. | 514/410 |
| 5,643,760 A | 7/1997 | Kojiri et al. | 435/85 |
| 5,654,427 A | 8/1997 | Dionne et al. | 540/545 |
| 5,668,152 A | 9/1997 | Heath, Jr. et al. | 514/323 |
| 5,668,271 A | 9/1997 | Kojiri et al. | 536/27.1 |
| 5,672,618 A | 9/1997 | Heath, Jr. et al. | 514/414 |
| 5,674,862 A | 10/1997 | Heath, Jr. et al. | 514/183 |
| 5,674,867 A | 10/1997 | Tamaoki et al. | 514/219 |
| 5,696,108 A | 12/1997 | Heath, Jr. et al. | 514/183 |
| 5,698,578 A | 12/1997 | Heath, Jr. et al. | 514/410 |
| 5,705,511 A | 1/1998 | Hudkins et al. | 514/338 |
| 5,710,145 A | 1/1998 | Engel et al. | 514/183 |
| 5,721,230 A | 2/1998 | Harris et al. | 514/214 |
| 5,721,272 A | 2/1998 | Faul et al. | 514/450 |
| 5,723,456 A | 3/1998 | Jirousek et al. | 514/183 |
| 5,728,709 A | 3/1998 | Ikuina et al. | 514/279 |
| 6,127,401 A | * 10/2000 | Singh et al. | 514/410 |

FOREIGN PATENT DOCUMENTS

| | | |
|---|---|---|
| EP | 0 238 011 A3 | 9/1987 |
| EP | 0 657 458 A1 | 6/1995 |
| EP | 0 768 311 A1 | 4/1997 |
| EP | 0 805 158 A2 | 11/1997 |
| JP | 7-112987 | 5/1995 |
| WO | WO 94/02488 | 2/1994 |
| WO | WO 96/30048 | 10/1996 |
| WO | WO 97/07081 | 2/1997 |
| WO | WO 97/18809 | 5/1997 |
| WO | WO 97/19080 | 5/1997 |
| WO | WO 97/21677 | 6/1997 |
| WO | WO 98/07433 | 2/1998 |

OTHER PUBLICATIONS

Angeles et al., "Enzyme–Linked Immunosorbent Assay for trkA Tyrosine Kinase Activity," *Anal. Biochem.*, 1996, 236, 49–55.

Aparico et al., "Synthesis and properties of some O–(2, 2–dialkoxyethyl)glycolaldehydes," *Carboydr. Res.*, 1983, 114, 297–302.

Bottenstein et al., "Growth of a rat neuroblastoma cell line in serum–free supplemented medium", *Proc. Natl. Acad. Sci. USA*, 1979, 76(1), 514–517.

Brenner, "The Synthesis of 2–Carboethoxy–Δ$^2$–cyclohexenone", *J. Org. Chem.*, 1961, 26, 22–27.

Denhardt, "Signal–transducing protein phosphorylation cascades mediated by Ras/Rho proteins in the mammalian cell: the potential for multiplex signalling," *Biochem. J.*, 1996, 318, 729–747.

Fonnum, "A rapid radiochemical method for the determination of choline acetyltransferase", *J. Neurochem.*, 1975, 24, 407–409.

Glicksman et al., "K–252a and Staurosporine Promote Choline Acetyltransferase Activity in Rat Spinal Cord Cultures," *J. Neurochem.*, 1993, 61(1), 210–221.

Grove et al., "Differential Activation and Inhibition of Lymphocyte Proliferation by Modulators of Protein Kinase C: Diacylglycereols, "Rationally Designed" Activators and Inhibitors of Protein Kinase C," *Exp. Cell Res.*, 1991, 193, 175–182.

Kase et al., "K–252a, A Potent Inhibitor of Protein Kinase C From Microbial Origin," *J. Antibiotics*, 1986, 39(8), 1059–1065.

(List continued on next page.)

Primary Examiner—Richard L. Raymond
(74) Attorney, Agent, or Firm—Woodcock Washburn LLP

(57) ABSTRACT

The present invention is directed to novel fused aryl and heteroaryl bridged indenopyrrolocarbazoles which are useful, inter alia, as therapeutic agents. The invention is also directed to methods for making and using the bridged indenopyrrolocarbazoles.

14 Claims, 9 Drawing Sheets

OTHER PUBLICATIONS

Khanna et al., "1,2–Diarylpyrroles as Potent and Selective Inhibitors of Cyclooxygenase–2," *J. Med. Chem.*, 1997, 40, 1619–1633.

Lehninger, *Biochemistry*, Second Edition, Worth Publishers, Inc., 1975, 73–75.

Martin–Zanca et al., "Molecular and Biochemical Characterization of the Human trk Proto–Oncogene," *Mol. Cell Biol.*, 1989, 9(1), 24–33.

McManaman et al., "Development Discord among Markers for Cholinergic Differentiation: In Vitro Courses for Early Expression and Responses to Skeletal Muscle Extract", *Devel. Biol.*, 1988, 125, 311–320.

Paquette et al., "First Synthesis of Cytotoxic 8,9–Secokaurene Diterpenoids. An Enantioselective Route to (–)–O–Methylshikoccin and (+)–O–Methylepoxyshikoccin," *J. Am. Chem. Soc.*, 1997, 119, 9662–9671.

Phelps et al., "Generation Patterns of Four Groups of Cholinergic Neurons in Rat Cervical Spinal Cord: A Combined Tritiated Thymidine Autoradiographic and Choline Acetyltransferase Immunocytochchemical Study," *J. Comp. Neurol.*, 1988, 273, 459–472.

Pitt et al., "High Throughput Screening Protein Kinase Assays Optimized for Reaction, Binding, and Detection Totally within a 96–Well Plate," *J. Biomol. Screening*, 1996, 1(1), 47–51.

Rotin et al., "SH2 domains prevent tyrosine dephosphorylation of the EGF receptor: identification of Tyr992 as the high–affinity binding site for SH2 domains of phospholipase Cγ," *EMBO J.*, 1992, 11(2), 559–567.

Schmidt et al., "The Total Synthesis of Antrimycin $D_v$; II:[1] Synthesis of Tetrahydropyridazinecarboxylic Acid and its Incorporation into Peptides," *Synthesis*, 1993, 809–814.

Smith et al., "Trophic Effects of Skeletal Muscle Extracts on Ventral Spinal Cord Neurons in Vitro: Separation of a Protein with Morphologic Activity from Proteins with Cholinergic Activity," *J. Cell Biology*, 1985, 101, 1608–1621.

Sworin et al., "Cyclopentanoid Synthesis via Directed Cationic Cyclizations. Efficient Generation and Rearrangement of the Intermediate Cyclohexyl Cation," *J. Org. Chem.*, 1988, 53, 4894–4896.

Wood, J.L. et al., "Total Synthesis of (+)–and (–)–K252a," *J. Am. Chem. Soc.*, 1995, 117, 10413–10414.

Xia et al., "Opposing Effects of ERK and JNK–p38 MAP Kinases on Apoptosis," *Science*, 1995, 270, 1326–1331.

Zirkle et al., "The Isomeric 3–Oxa–and 3–Thiagranatanin–7–ols and Their Derivatives; Reduction of Bicyclic Amino Ketones Related to Tropinone," *J. Org. Chem.*, 1961, 26, 395–407.

Green and Wuts, *Protective Group in Organic Synthesis*, 2d. Edition, Wiley & Sons, 1991.

Remington's Sciences, Mack Publishing Co., Easton, PA 1980.

* cited by examiner

BRIDGED INDENOPYRROLOCARBAZOLES

This Application: is a divisional of application Ser. No. 09/325,140 filed Jun. 3, 1999, now U.S. Pat. No. 6,127,401, which claims benefit of U.S. Provisional Application Ser. No. 60/088,114, filed Jun. 5, 1998.

FIELD OF INVENTION

The present invention is directed to novel fused aryl and heteroaryl bridged indenopyrrolocarbazoles, which are referred to herein as "bridged indenopyrrolocarbazoles." The invention also is directed to methods for making and using the bridged indenopyrrolocarbazoles.

BACKGROUND OF THE INVENTION

The microbial-derived material referred to as "K-252a" is a unique compound which has gained significant attention over the past several years due to the variety of functional activities which it possesses. K-252a is an indolocarbazole alkaloid that was originally isolated from a Nocardiosis sp. culture (Kase, H et al. 39 *J. Antibiotics* 1059, 1986). K-252a is an inhibitor of several enzymes, including protein kinase C (PKC) which plays a central role in regulating cell functions, and trk tyrosine kinase. The reported functional activities of K-252a and its derivatives are numerous and diverse: tumor inhibition (See U.S. Pat. Nos. 4,877,776, 4,923,986, and 5,063,330; European Publication 238,011 in the name of Nomato); anti-insecticidal activity (See U.S. Pat. No. 4,735,939); inhibition of inflammation (See U.S. Pat. No. 4,816,450); treatment of diseases associated with neuronal cells (See U.S. Pat. Nos. 5,461,146; 5,621,100; 5,621,101; and WIPO Publication WO 94/02488, published Feb. 3, 1994 in the names of Cephalon, Inc. and Kyowa Hakko Kogyo Co., Ltd.); and treatment of prostate disease (See U.S. Pat. Nos. 5,516,771; and 5,654,427). K-252a also has been reported to inhibit IL-2 production (See Grove, D. S. et al., Experimental Cell Research 193: 175–182, 1991).

The reported indolocarbazoles share several common attributes. In particular, each comprises three five member rings which all include a nitrogen moiety; staurosporine (derived from Streptomyces sp.) and K-252a each further comprise a sugar moiety linked via two N-glycosidic bonds. Both K-252a and staurosporine have been extensively studied with respect to their utility as therapeutic agents. The indolocarbazoles are generally lypophilic which allows for their comparative ease in crossing biological membranes, and, unlike proteinaceous materials, they manifest a longer in vivo half life.

Although K-252a is normally derived from culture media via a fermentation process, the total synthesis of the natural (+) isomer and the unnatural (−) isomer, in which the three chiral carbons of the sugar have the opposite configurations, has been achieved (See Wood et al., J. Am. Chem. Soc. 117: 10413, 1995, and WIPO Publication WO 97/07081). However, this synthesis is not practical for commercial use.

In addition to the indolocarbazole alkaloids represented by K-252a and staurosporine, synthetic small organic molecules which are biologically active and known as fused pyrrolocarbazoles have been prepared (See U.S. Pat. Nos. 5,475,110; 5,591,855; 5,594,009; 5,705,511; and 5,616,724).

Fused isoindolones which are non-indole-containing molecules that can be chemically synthesized de novo are also known (See WIPO Publication WO 97/21677).

Certain bis-indolylmaleimide macrocyclic derivatives have also been reported (See for example U.S. Pat. Nos. 5,710,145; 5,672,618; 5,552,396; and 5,545,636).

Sugar derivatives of indolopyrrolocarbazoles also have been reported (see WIPO Publication WO98/07433).

There remains a need for novel pyrrolocarbazole derivatives that possess beneficial properties. This invention is directed to this, as well as other, important ends.

SUMMARY OF THE INVENTION

The present invention is directed to novel fused aryl and heteroaryl bridged indenopyrrolocarbazoles, which are referred to herein as "bridged indenopyrrolocarbazoles." Exemplary compounds of the invention have the general Formula I:

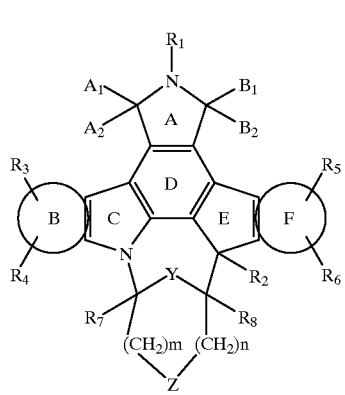

I

Constituent members and preferred embodiments are disclosed in detail infra. The compounds are useful, inter alia, for enhancing trophic factor-induced activities of trophic factor responsive cells, e.g., cholinergic neurons, and may also function as survival-promoting agents for other neuronal cell types, e.g., dopaminergic and glutamatergic, and are thus beneficial pharmacological and therapeutic agents. The present compounds are also useful in the treatment of disorders associated with decreased ChAT activity or the death or injury to spinal cord motoneurons, and also have utility in diseases associated with apoptotic cell death of the central and peripheral nervous system, immune system, and in inflammatory diseases.

The certain bridged indenopyrrolocarbazole compounds described herein may also find utility in the treatment of disease states involving malignant cell proliferation, such as cancer.

Compositions containing the subject compounds, and methods for using the subject compounds, are disclosed. Methodologies for making the present bridged indenopyrrolocarbazoles are also disclosed. Other useful methodologies will be apparent to those skilled in the art, once armed with the present disclosure. These and other features of the compounds of the subject invention are set forth in more detail below.

DETAILED DESCRIPTION

Figure 1:
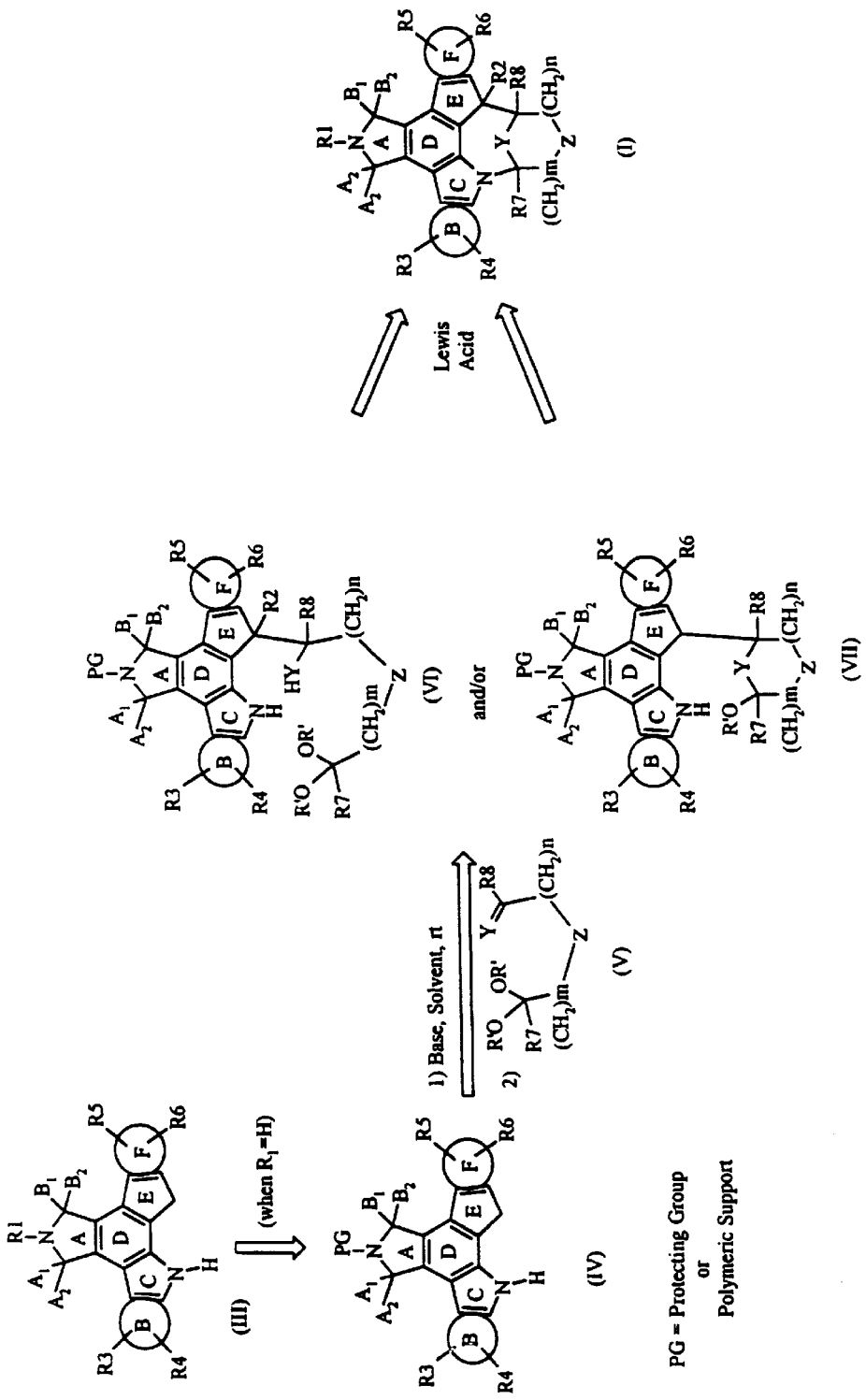
FIG. 1 is a schematic drawing showing a general preparation of bridged indenopyrrolocarbazoles.

Disclosed herein are bridged indenopyrrolocarbazoles which are represented by the following Formula I:

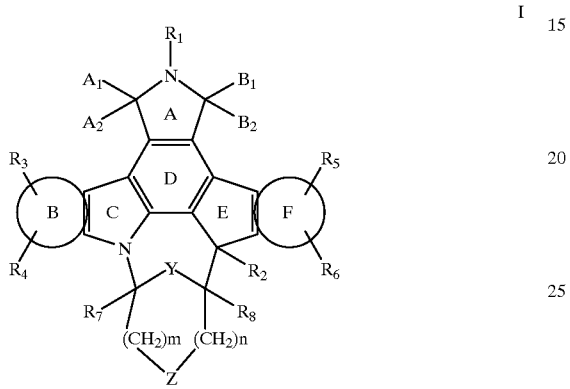

wherein:
ring B and ring F, independently, and each together with the carbon atoms to which they are attached, are selected from the group consisting of:
a) an unsaturated 6-membered carbocyclic aromatic ring in which from 1 to 3 carbon atoms may be replaced by nitrogen atoms;
b) an unsaturated 5-membered carbocyclic aromatic ring; and
c) an unsaturated 5-membered carbocyclic aromatic ring in which either
1) one carbon atom is replaced with an oxygen, nitrogen, or sulfur atom;
2) two carbon atoms are replaced with a sulfur and a nitrogen atom, an oxygen and a nitrogen atom, or two nitrogen atoms; or
3) three carbon atoms are replaced with three nitrogen atoms;

$R^1$ is selected from the group consisting of:
a) H, substituted or unsubstituted alkyl having from 1 to 4 carbons, substituted or unsubstituted aryl, substituted or unsubstituted arylalkyl, substituted or unsubstituted heteroaryl, or substituted or unsubstituted heteroarylalkyl;
b) —C(=O)$R^9$, where $R^9$ is selected from the group consisting of alkyl, aryl and heteroaryl;
c) —OR$^{10}$, where $R^{10}$ is selected from the group consisting of H and alkyl having from 1 to 4 carbons;
d) —C(=O)NH$_2$, —NR$^{11}$R$^{12}$, —(CH$_2$)$_p$NR$^{11}$R$^{12}$, —(CH$_2$)$_p$OR$^{10}$, —O(CH$_2$)$_p$OR$^{10}$ and —O(CH$_2$)$_p$NR$^{11}$R$^{12}$, wherein p is from 1 to 4; and wherein either
1) $R^{11}$ and $R^{12}$ are each independently selected from the group consisting of H and alkyl having from 1 to 4 carbons; or
2) $R^{11}$ and $R^{12}$ together form a linking group of the formula —(CH$_2$)$_2$—X$^1$—(CH$_2$)$_2$—, wherein X$^1$ is selected from the group consisting of —O—, —S—, and —CH$_2$—;

$R^2$ is selected from the group consisting of H, alkyl having from 1 to 4 carbons, —OH, alkoxy having from 1 to 4 carbons, —OC(=O)R$^9$, —OC(=O)NR$^{11}$R$^{12}$, —O(CH$_2$)$_p$NR$^{11}$R$^{12}$, —O(CH$_2$)$_p$OR$^{10}$, substituted or unsubstituted arylalkyl having from 6 to 10 carbons, and substituted or unsubstituted heteroarylalkyl;

$R^3$, $R^4$, $R^5$ and $R^6$ are each independently selected from the group consisting of:
a) H, aryl, heteroaryl, F, Cl, Br, I, —CN, CF$_3$, —NO$_2$, —OH, —OR$^9$, —O(CH$_2$)$_p$NR$^{11}$R$^{12}$, —OC(=O)R$^9$, —OC(=O)NR$^2$R$^7$, —OC(=O)NR$^{11}$R$^{12}$, —O(CH$_2$)$_p$OR$^{10}$, —CH$_2$OR$^{10}$, —NR$^{11}$R$^{12}$, —NR$^{10}$S(=O)$_2$R$_9$, —NR$^{10}$C(=O)R$^9$,
b) —CH$_2$OR$^{14}$, wherein R$^{14}$ is the residue of an amino acid after the hydroxyl group of the carboxyl group is removed;
c) —NR$^{10}$C(=O)NR$^{11}$R$^{12}$, —CO$_2$R$^2$, —C(=O)R$^2$, —C(=O)NR$^{11}$R$^{12}$, —CH=NOR$^2$, —CH=NR$^9$, —(CH$_2$)$_p$NR$^{11}$R$^{12}$, —(CH$_2$)$_p$NHR$^{14}$, or —CH=NNR$^2$R$^{2A}$ wherein R$^{2A}$ is the same as R$^2$;
d) —S(O)$_y$R$^2$ —(CH$_2$)$_p$S(O)$_y$R$^9$, —CH$_2$S(O)$_y$R$^{14}$ wherein y is 0,1 or 2;
e) alkyl having from 1 to 8 carbons, alkenyl having from 2 to 8 carbons, and alkynyl having 2 to 8 carbons, wherein
1) each alkyl, alkenyl, or alkynyl group is unsubstituted; or
2) each alkyl, alkenyl, or alkynyl group is substituted with 1 to 3 groups selected from the group consisting of aryl having from 6 to 10 carbons, heteroaryl, arylalkoxy, heterocycloalkoxy, hydroxyalkoxy, alkyloxy-alkoxy, hydroxyalkylthio, alkoxy-alkylthio, F, Cl, Br, I, —CN, —NO$_2$, —OH, —OR$^9$, —X$^2$(CH$_2$)$_p$NR$^{11}$R$^{12}$, —X$^2$(CH$_2$)$_p$C(=O)NR$^{11}$R$^{12}$, —X$^2$(CH$_2$)$_p$OC(=O)NR$^{11}$R$^{12}$, —X$^2$(CH$_2$)$_p$CO$_2$R$^9$, —X$^2$(CH$_2$)$_p$S(O)$_y$R$^9$, —X$^2$(CH$_2$)$_p$NR$^{10}$C(=O)NR$^{11}$R$^{12}$, —OC(=O)R$^9$, —OCONHR$^2$, —O-tetrahydropyranyl, —NR$^{11}$R$^{12}$, —NR$^{10}$C(=O)R$^9$, NR$^{10}$CO$_2$R$^9$, —NR$^{10}$C(=O)NR$^{11}$R$^{12}$, —NHC(=NH)NH$_2$, NR$^{10}$S(O)$_2$R$^9$, —S(O)$_y$R$^9$, —CO$_2$R$^2$, —C(=O)NR$^{11}$R$^{12}$, —C(=O)R$^2$, —CH$_2$OR$^{10}$, —CH=NNR$^2$R$^{2A}$, —CH=NOR$^2$, —CH=NR$^9$, —CH=NNHCH(N=NH)NH$_2$, —S(=O)$_2$NR$^2$R$^{2A}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons;
X$^2$ is O, S, or NR$^{10}$;

$R^7$ and $R^8$ are each independently selected from the group consisting of H, alkyl having from 1 to 4 carbons, alkoxy having from 1 to 4 carbons, substituted or unsubstituted arylalkyl having from 6 to 10 carbons, substituted or unsubstituted heteroarylalkyl, —(CH$_2$)$_p$OR$^{10}$, —(CH$_2$)$_p$OC(=O)NR$^{11}$R$^{12}$, and —(CH$_2$)$_p$NR$^{11}$R$^{12}$; or $R^7$ and $R^8$ together form a linking group of the formula —CH$_2$—X$^3$—CH$_2$—, wherein X$^3$ is X$^2$ or a bond;

m and n are each independently 0, 1, or 2;

Y is selected from the group consisting of —O—, —S—, —N(R$^{10}$)—, —N$^+$(O$^-$)(R$^{10}$)—, —N(OR$^{10}$)—, and —CH$_2$—;

Z is selected from the group consisting of a bond, —O—, —CH=CH—, —S—, —C(=O)—, —CH(OR$^{10}$)—, —N(R$^{10}$)—, —N(OR$^{10}$)—, CH(NR$^{11}$R$^{12}$)—, —C(=O)N(R$^{17}$)—, —N(R$^{17}$)C(=O)—, —N(S(O)$_y$R$^9$)—, —N(S(O)$_y$NR$^{11}$R$^{12}$)—, —N(C(=O)R$^{17}$)—, —C(R$^{15}$R$^{16}$)—, —N$^+$(O$^-$)(R$^{10}$)—, —CH(OH)—CH(OH)—, and —CH(O(C=O)R$^9$)CH(OC(=O)R$^{9A}$)—, wherein R$^{9A}$ is the same as R$^9$;

R$^{15}$ and R$^{16}$ are independently selected from the group consisting of H, —OH, —C(=O)R$^{10}$, —O(C=O)R$^9$, hydroxyalkyl, and —CO$_2$R$^{10}$;

R$^{17}$ is selected from the group consisting of H, alkyl, aryl, and heteroaryl;

A$^1$ and A$^2$ are selected from the group consisting of H, H; H, OR$^2$; H, —SR$^2$; H, —N(R$^2$)$_2$; and a group wherein A$^1$ and A$^2$ together form a moiety selected from the group consisting of =O, =S, and =NR$^2$;

B$^1$ and B$^2$ are selected from the group consisting of H, H; H, —OR$^2$; H, —SR$^2$; H, —N(R$^2$)$_2$; and a group wherein B$^1$ and B$^2$ together form a moiety selected from the group consisting of =O, =S, and =NR$^2$;

with the proviso that at least one of the pairs A$^1$ and A$^2$, or B$^1$ and B$^2$, form =O. The compounds of the invention includes all diasteriomers and enantiomers around the carbon atoms to which the substituents R$^2$, R$^7$, and R$^8$ are attached.

Preferred bridged indenopyrrolocarbazoles are represented by the following formula:

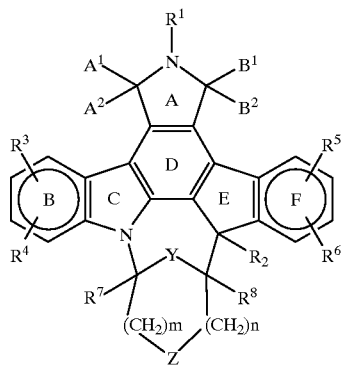

II

In some preferred embodiments of the compounds of Formula II, the compounds have diastereomers of formula:

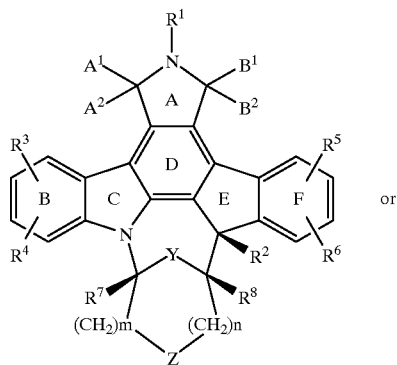

or

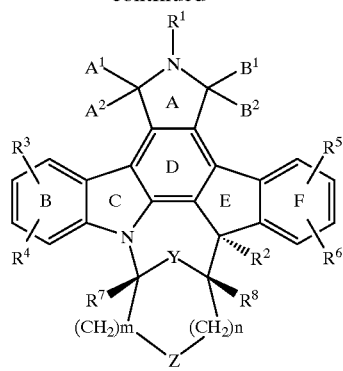

In other preferred embodiments of the compounds of Formula II, the compounds have enantiomers of the formula:

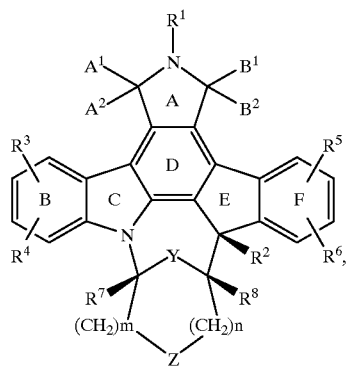

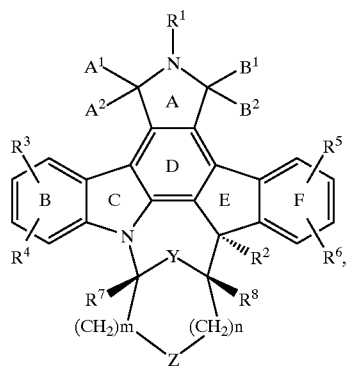

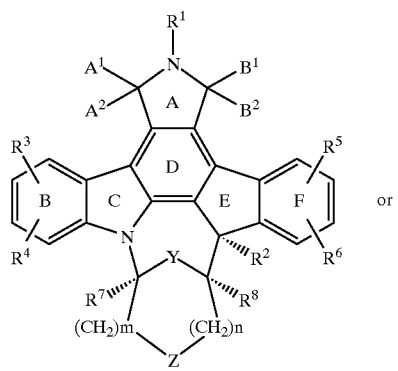

or

-continued

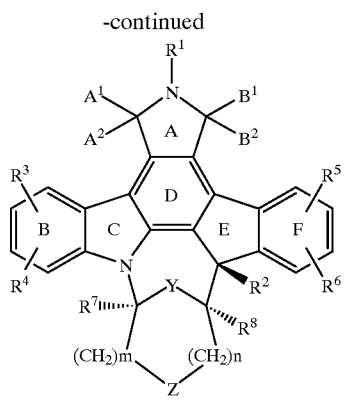

In some preferred embodiments of the compounds of Formula I and II, $R^1$ is H. In further preferred embodiments, $R^2$, is H, hydroxyl, or substituted or unsubstituted alkyl.

In other preferred embodiments, $R^3$, $R^4$, $R^5$, and $R^6$ are independently H, substituted or unsubstituted alkyl, halogen, substituted or unsubstituted alkoxy, substituted or unsubstituted amino, or substituted or unsubstituted aryl. In further preferred embodiments, $R^7$ and $R^8$ are independently H, or substituted or unsubstituted alkyl.

In some preferred embodiments, Y is O. In further preferred embodiments Z is a bond, O, S, or substituted or unsubstituted N. In still further preferred embodiments, m and n are independently 1 or 2. In some especially preferred embodiments, Y is O, Z is a bond or O, and m and n are independently 1 or 2. In further preferred embodiments, $A^1A^2$ and $B^1B^2$ are independently =O or H,H.

In some especially preferred embodiments, $R^1$, $R^4$, $R^6$, and $R^7$ are each H, Y is =O, n is 1, $A^1A^2$ and $B^1B^2$ are =O or H,H, $R^2$ is H, OH or lower alkyl, $R^3$ is H or substituted alkyl, $R^5$ and $R^8$ are each H or alkoxy, with methoxy being preferred, Z is a bond or O, and m is 1 or 2.

In other preferred embodiments, compounds of Formula II have the formula:

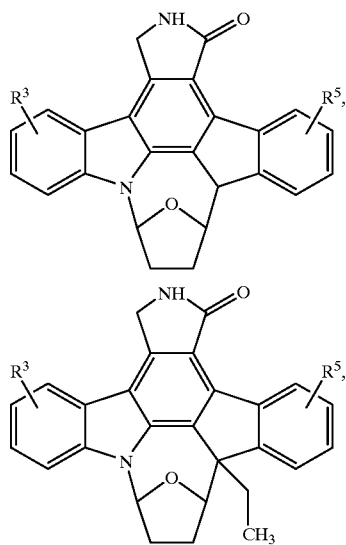

-continued

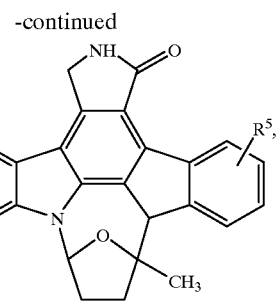

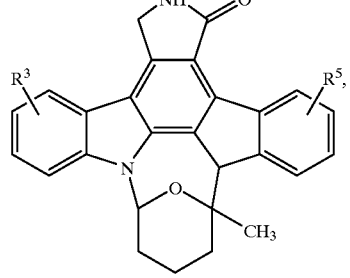

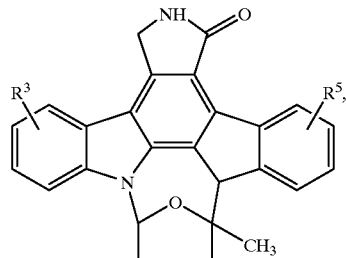

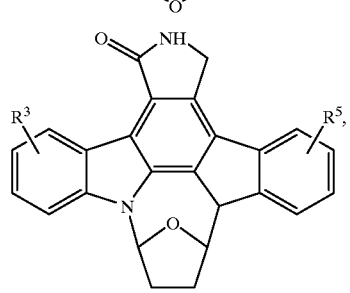

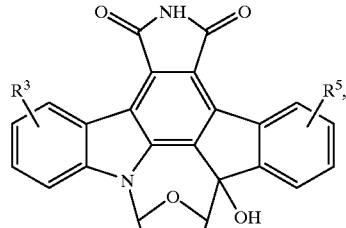

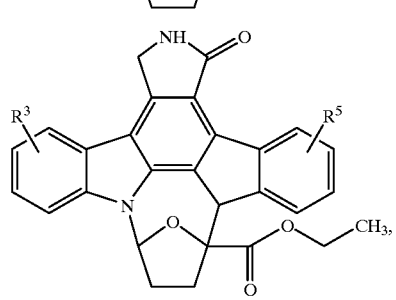

-continued

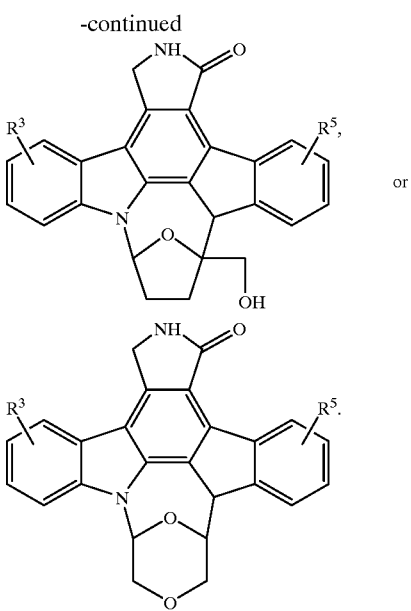

In more preferred embodiments, $R^3$ and $R^5$ are each independently selected from the group consisting of:

a) H, heteroaryl, F, Br, —CN, $CF_3$, —$NO_2$, —OH, —$OR^9$, —$O(CH_2)_pNR^{11}R^{12}$, —$OC(=O)R^9$, —$OC(=O)NR^2R^7$, —$OC(=O)NR^{11}R^{12}$, —$O(CH_2)_pOR^{10}$, —$CH_2OR^{10}$, —$NR^{11}R^{12}$, —$NR^{10}S(=O)_2R^9$, —$NR^{10}C(=O)R^9$;

c) —$NR^{10}C(=O)NR^{11}R^{12}$, —$CO_2R^2$, —$C(=O)R^2$, —$C(=O)NR^{11}R^{12}$, —CH=$NOR^2$; —CH=$NR^9$, —$(CH_2)_pNR^{11}R^{12}$, —$(CH_2)_pNHR^{14}$;

d) —$S(O)_yR^2$ —$(CH_2)_pS(O)_yR^9$, —$CH_2S(O)_yR^{14}$ wherein y is 0, 1 or 2; and e) alkyl having from 1 to 8 carbons, alkenyl having from 2 to 8 carbons, and alkynyl having 2 to 8 carbons, wherein
  1) each alkyl, alkenyl, or alkynyl group is unsubstituted; or
  2) each alkyl, alkenyl, or alkynyl group is substituted with 1 to 3 groups selected from the group consisting of aryl having from 6 to 10 carbons, heteroaryl, arylalkoxy, heterocycloalkoxy, hydroxyalkoxy, alkyloxy-alkoxy, hydroxyalkylthio, alkoxyalkylthio, F, Cl, Br, I, —CN, —$NO_2$, —OH, —$OR^9$, —$X^2(CH_2)_pNR^{11}R^{12}$, —$X^2(CH_2)_pC(=O)NR^{11}R^{12}$, —$X^2(CH_2)_pOC(=O)NR^{11}R^{12}$, —$X^2(CH_2)_pCO_2R^9$, —$X^2(CH_2)_pS(O)_yR^9$, —$X^2(CH_2)_pNR^{10}C(=O)NR^{11}R^{12}$, —$OC(=O)R^9$, —$OCONHR^2$, —O-tetrahydropyranyl, —$NR^{11}R^{12}$, —$NR^{10}C(=O)R^9$, —$NR^{10}CO_2R^9$, —$NR^{10}C(=O)NR^{11}R^{12}$, —$NHC(=NH)NH_2$, $NR^{10}S(O)_2R^9$, —$S(O)_yR^9$, —$CO_2R^2$, —$C(=O)NR^{11}R^{12}$, —$C(=O)R^2$, —$CH_2OR^{10}$, —CH=$NR^9$, —$S(=O)_2NR^2R^{2A}$, —$OR^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from of 1 to 4 carbons.

In even more preferred embodiments, $R^5$ is independently selected from the group consisting of H, —$OR^9$, —$O(CH_2)_pNR^{11}R^{12}$, —$OC(=O)R^9$, —$OC(=O)NR^2R^7$, —$OC(=O)NR^{11}R^{12}$, —$O(CH_2)_pOR^{10}$, —$CH_2OR^{10}$, —$NR^{11}R^{12}$, —$NR^{10}S(=O)_2R^9$, —$NR^{10}C(=O)R^9$, —$C(=O)NR^{11}R^{12}$, —$(CH_2)_pNR^{11}R^{12}$, —$S(O)_yR^2$, —$(CH_2)_pS(O)_yR^9$, and —$CH_2S(O)_yR^{14}$ wherein y is 0, 1 or 2.

Some especially preferred embodiments of the compounds of Formula II are compounds II-1, II-1b, II-2, II-3, II-4a, II-4b, II-5, II-6, II-7a, II-7b, II-8, II-9, II-10, II-11, II-12, II-13, II-14a, II-14b, II-15, II-16a, and II-16b, the structures of which are set forth in Table 8, infra. Certain preferred chirally specific embodiments of the compounds of Formula II are set forth in Table 9, infra.

In other embodiments, the present invention provides pharmaceutical compositions comprising a compound of Formula I or Formula II and a pharmaceutically acceptable carrier.

In certain preferred pharmaceutical compositions, the composition is for inhibiting one or more of trk kinase activity, VEGFR kinase activity, or PDGFR activity wherein the composition comprises a compound of Formula I and a pharmaceutically acceptable carrier. In other preferred pharmaceutical compositions, the composition is for enhancing tropic factor or spinal chord ChAT activity wherein the composition comprises a compound of Formula I and a pharmaceutically acceptable carrier.

In other preferred pharmaceutical compositions, the composition is for treating or preventing prostate disorders such as prostate cancer or benign prostate hyperplasia. In other preferred pharmaceutical compositions, the composition is for treating or preventing angiogenic disorders such as cancer of solid tumors, endometriosis, diabetic retinopathy, psoriasis, hemangioblastoma, ocular disorders or macular degeneration. In other preferred pharmaceutical compositions, the composition is for treating or preventing neoplasia, rheumatoid arthritis, pulmonary fibrosis, myelofibrosis, abnormal wound healing, atherosclerosis, or restenosis. In other preferred pharmaceutical compositions, the composition is for treating or preventing Alzheimer's disease, amyotrophic lateral sclerosis, Parkinson's disease, stroke, ischaemia, Huntington's disease, AIDS dementia, epilepsy, multiple sclerosis, peripheral neuropathy, or injuries of the brain or spinal chord.

In other embodiments, the present invention provides a method for inhibiting trk kinase activity comprising providing a compound of Formula I in an amount sufficient to result in effective inhibition. In a preferred embodiment, the compound of Formula I is provided to treat inflammation. In another preferred embodiment, the trk kinase receptor is trk A.

In other embodiments, the present invention provides a method for treating or preventing prostate disorders which comprises administering to a host in need of such treatment or prevention a therapeutically effective amount of a compound of Formula I. In a preferred embodiment, the prostate disorder is prostate cancer or benign prostate hyperplasia.

In other embodiments, the present invention provides a method for treating or preventing angiogenic disorders where VEGFR kinase activity contributes to pathological conditions comprising providing a compound of Formula I in an amount sufficient to result in the vascular endothelial growth factor receptor being contacted with an effective inhibitory amount of the compound. In another embodiment, the present invention provides a method for treating or preventing angiogenic disorders which comprises administering to a host in need of such treatment or prevention a therapeutically effective amount of a compound of Formula I. In a preferred embodiment, the angiogenic disorder is cancer of solid tumors, ocular disorders, macular degeneration, endometriosis, diabetic retinopathy, psoriasis, or hemangioblastoma.

In other embodiments, the present invention provides a method for treating or preventing disorders where PDGFR activity contributes to pathological conditions comprising providing a compound of Formula I in an amount sufficient to result in the platelet derived growth factor receptor being contacted with an effective inhibitory amount of the compound. In another embodiment, the present invention provides a method for treating or preventing pathological disorders which comprises administering to a host in need of such treatment or prevention a therapeutically effective amount of a compound of Formula I. In preferred embodiments, the pathological disorder is neoplasia, rheumatoid arthritis, pulmonary fibrosis, myelofibrosis, abnormal wound healing, atherosclerosis, or restenosis.

In other embodiments, the present invention provides a method for treating disorders characterized by the aberrant activity of trophic factor responsive cells comprising providing a compound of Formula I in an amount sufficient to result in the trophic factor cell receptor being contacted with an effective activity inducing amount of the compound. In preferred embodiments, the activity of the trophic factor responsive cells is ChAT activity. In another embodiment, the present invention provides a method for treating or preventing Alzheimer's disease, amyotrophic lateral sclerosis, Parkinson's disease, stroke, ischaemia, Huntington's disease, AIDS dementia, epilepsy, multiple sclerosis, peripheral neuropathy, or injuries of the brain or spinal chord which comprises administering to a host in need of such treatment or prevention a therapeutically effective amount of a compound of Formula I.

The compounds of the present invention include all diastereomers and enantiomers. Compounds of Formula (I) are also referred to herein as Compound (I), and the same applies to the compounds of other formula numbers.

As used herein, the term "carbocyclic" refers to cyclic groups in which the ring portion is composed solely of carbon atoms. The terms "heterocyclo" and "heterocyclic" refer to cyclic groups in which the ring portion includes at least one heteroatom such as O, N, or S.

As used herein, the term "alkyl" means a straight-chain, cyclic, or branched alkyl group having 1 to 8 carbon atoms, such as methyl, ethyl, propyl, isopropyl, butyl, isobutyl, sec-butyl, tert-butyl, pentyl, isoamyl, neopentyl, 1-ethylpropyl, hexyl, octyl, cyclopropyl, and cyclopentyl. The alkyl moiety of alkyl-containing groups, such as alkoxy, alkoxycarbonyl, and alkylaminocarbonyl groups, has the same meaning as alkyl defined above. Lower alkyl groups, which are preferred, are alkyl groups as defined above which contain 1 to 4 carbons. The term "alkenyl" is intended to include straight-chain or branched hydrocarbon chains having at least one carbon-carbon double bond. Examples of alkenyl groups include ethenyl and propenyl groups. As used herein, the term "alkynyl" is intended to include straight-chain or branched hydrocarbon chains having at least one carbon-carbon triple bond. Examples of alkynyl groups include ethynyl and propynyl groups.

The acyl moiety of acyl-containing groups such as acyloxy groups is intended to include a straight-chain or branched alkanoyl group having 1 to 6 carbon atoms, such as formyl, acetyl, propanoyl, butyryl, valeryl, pivaloyl or hexanoyl.

As used herein the term "aryl" means a group having 6 to 12 carbon atoms such as phenyl, biphenyl and naphthyl. Preferred aryl groups include unsubstituted or substituted phenyl and naphthyl groups. The term "heteroaryl" as used herein denotes an aryl group in which one or more ring carbon atom is replaced by a hetero (i.e., non-carbon) atom such as O, N or S. Preferred heteroaryl groups include pyridyl, pyrimidyl, pyrrolyl, furyl, thienyl, imidazolyl, triazolyl, tetrazolyl, quinolyl, isoquinolyl, benzoimidazolyl, thiazolyl, pyrazolyl, and benzothiazolyl groups.

The term "aralkyl" (or "arylalkyl") is intended to denotes a group having from 7 to 15 carbons, consisting of an alkyl group that bears an aryl group. Examples of aralkyl groups include benzyl, phenethyl, benzhydryl and naphthylmethyl groups. Alkyl groups and alkyl moieties contained within substituent groups such as aralkyl, alkoxy, arylalkoxy, hydroxyalkyl, alkoxy-alkoxy, hydroxy-alkylthio, alkoxyalkylthio, alkylcarbonyloxy, hydroxyalkyl and acyloxy groups may be substituted or unsubstituted. A substituted alkyl group has 1 to 3 independently-selected substituents, preferably hydroxy, lower alkoxy, lower alkoxy-alkoxy, substituted or unsubstituted arylalkoxy-lower alkoxy, substituted or unsubstituted heteroarylalkoxy-lower alkoxy, substituted or unsubstituted arylalkoxy, substituted or unsubstituted heterocycloalkoxy, halogen, carboxyl, lower alkoxycarbonyl, nitro, amino, mono- or di-lower alkylamino, dioxolane, dioxane, dithiolane, dithione, furan, lactone, or lactam.

Substituted aryl, substituted heteroaryl and substituted aralkyl groups each have 1 to 3 independently-selected substituents that are preferably lower alkyl, hydroxy, lower alkoxy, carboxy, lower alkoxycarbonyl, nitro, amino, mono- or di-lower alkylamino, and halogen.

Heterocyclic groups formed with a nitrogen atom include pyrrolidinyl, piperidinyl, piperidino, morpholinyl, morpholino, thiomorpholino, N-methylpiperazinyl, indolyl, isoindolyl, imidazole, imidazoline, oxazoline, oxazole, triazole, thiazoline, thiazole, pyrazole, pyrazolone, and triazole groups. Heterocyclic groups formed with an oxygen atom includes furan, tetrahydrofuran, pyran, and tetrahydropyran groups.

"Hydroxyalkyl" groups are alkyl groups that have a hydroxyl group appended thereto. Halogens include fluorine, chlorine, bromine and iodine.

As used herein, the term "heteroarylalkyl" means an arylaklyl group that contains a heteroatom. The term "oxy" denotes the presence of an oxygen atom. Thus, "alkoxy" groups are alkyl groups that are attached through an oxygen atom, and "carbonyloxy" groups are carbonyl groups that are attached through an oxygen atom.

The term "heterocycloalkoxy" means an alkoxy group that has a heterocyclo group attached to the alkyl moiety thereof, and the term "arylalkoxy" means an alkoxy group that has an aryl group attached to the alkyl moiety thereof. The term "alkylcarbonyloxy" means an group of formula —O—C(=O)-alkyl.

As used herein, the term "alkyloxy-alkoxy" denotes an alkoxy group that contains an alkyloxy substituent attached to its alkyl moiety. The term "alkoxy-alkylthio" means an alkylthio group (i.e., a group of formula —S-alkyl) that contains an alkoxy substituent attached to its alkyl moiety. The term "hydroxy-alkylthio" means an alkylthio group (i.e., a group of formula —S-alkyl) that contains a hydroxy substituent attached to its alkyl moiety.

As used herein, the term "monosaccharide" has its accustomed meaning as a simple sugar.

As used herein, the term "amino acid" denotes a molecule containing both an amino group and a carboxyl group. Embodiments of amino acids include α-amino acids; i.e., carboxylic acids of general formula HOOC—CH(NH$_2$)—(side chain).

Side chains of amino acids include naturally occurring and non-naturally occurring moieties. Non-naturally occurring (i.e., unnatural) amino acid side chains are moieties that are used in place of naturally occurring amino acid side chains in, for example, amino acid analogs. See, for example, Lehninger, *Biochemistry,* Second Edition, Worth Publishers, Inc, 1975, pages 73–75, incorporated by reference herein.

Preferred α-amino acids include glycine, alanine, proline, glutamic acid, and lysine, having the D configuration, the L configuration, or as a racemate.

The sidechains of further representative α-amino acids are shown below in Table 1.

TABLE 1

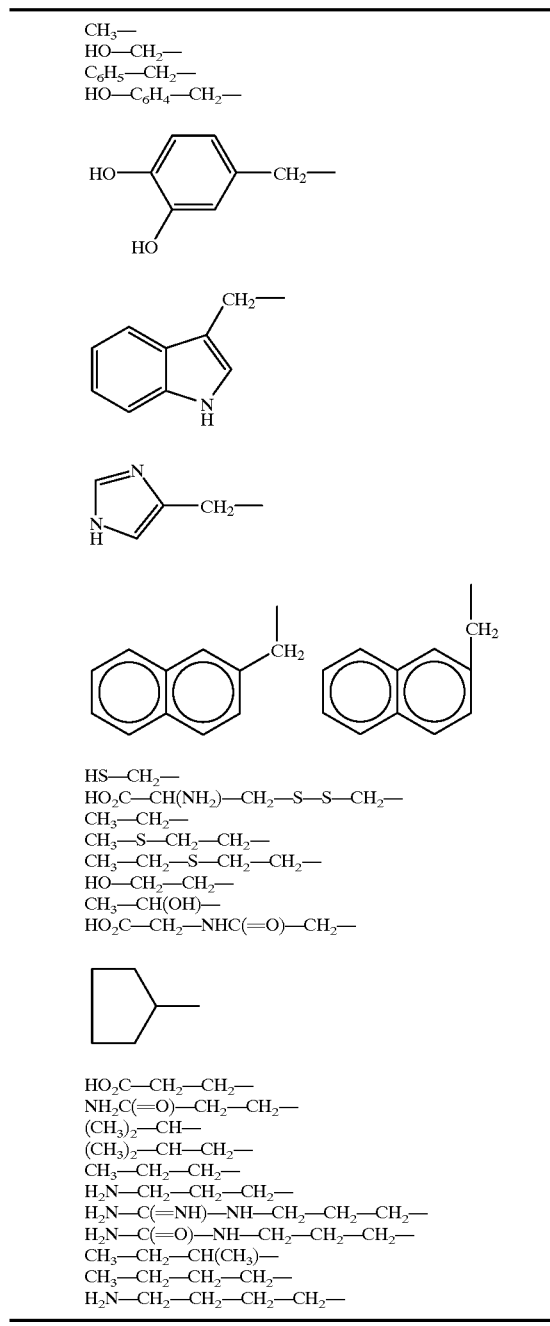

In some preferred embodiments, substituent groups for the compounds of Formulas I and II include the residue of an amino acid after removal of the hydroxyl moiety of the carboxyl group thereof; i.e., groups of Formula —C(=O)—CH(NH$_2$)—(side chain).

Functional groups present on the compounds of Formula I may contain protecting groups. For example, the amino acid sidechain substituents of the compounds of Formula I can be substituted with protecting groups such as benzyloxycarbonyl or t-butoxycarbonyl groups. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. One such protecting group is the benzyloxycarbonyl (Cbz; Z) group. Other preferred protecting groups according to the invention may be found in Greene, T. W. and Wuts, P. G. M., *"Protective Groups in Organic Synthesis"* 2d. Ed., Wiley & Sons, 1991.

The bridged indenopyrrolocarbazole compounds have evidenced important functional pharmacological activities which find utility in a variety of settings, including both research and therapeutic arenas. These derivatives are useful as therapeutic agents. The activities of the compounds show positive effects on the function and/or survival of trophic factor responsive cells. Effect on the function and/or survival of trophic factor responsive cells, e.g., cells of a neuronal lineage, has been demonstrated using any of the following assays: (1) cultured spinal cord choline acetyltransferase ("ChAT") assay; or (2) cultured basal forebrain neuron ChAT activity assay.

As used herein, the term "effect" when used to modify the terms "function" and "survival" means a positive or negative alteration or change. An effect which is positive can be referred to herein as an "enhancement" or "enhancing" and an effect which is negative can be referred to herein as "inhibition" or "inhibiting."

As used herein, the terms "enhance" or "enhancing" when used to modify the terms "function" or "survival" means that the presence of a bridged indenopyrrolocarbazole compound has a positive effect on the function and/or survival of a trophic factor responsive cell compared with a cell in the absence of the compound. For example, and not by way of limitation, with respect to the survival of, e.g., a cholinergic neuron, the compound would evidence enhancement of survival of a cholinergic neuronal population at risk of dying (due to, e.g., injury, a disease condition, a degenerative condition or natural progression) when compared to a cholinergic neuronal population not presented with such compound, if the treated population has a comparatively greater period of functionality than the non-treated population.

As used herein, "inhibit" and "inhibition" mean that a specified response of a designated material (e.g., enzymatic activity) is comparatively decreased in the presence of a bridged indenopyrrolocarbazole compound.

As used herein, the term "trk" refers to the family of high affinity neurotrophin receptors presently comprising trk A, trk B, and trk C, and other membrane associated proteins to which a neurotrophin can bind.

As used herein, inhibition of VEGFR implies utility in, for example, diseases where angiogenesis plays important roles, such as cancer of solid tumors, endometriosis, diabetic retinopathy, psoriasis, hemangioblastoma, as well as other ocular diseases and cancers.

Inhibition of trk implies utility in, for example, diseases of the prostate such as prostate cancer and benign prostate hyperplasia, and treatment of inflammatory pain.

Inhibition of Platelet Derived Growth Factor Receptor (PDGFR) implies utility in, for example, various forms of neoplasia, rheumatoid arthritis, pulmonary fibrosis, myelofibrosis, abnormal wound healing, diseases with cardiovascular end points, such as atherosclerosis, restenosis, post-angioplasty restenosis, etc.

As used herein, the terms "cancer" and "cancerous" refer to any malignant proliferation of cells in a mammal. Examples include prostate, benign prostate hyperplasia, ovarian, breast, brain, lung, pancreatic, colorectal, gastric, stomach, solid tumors, head and neck, neuroblastoma, renal cell carcinoma, lymphoma, leukemia, other recognized malignancies of the hematopoietic systems, and other recognized cancers.

As used herein the terms "neuron," "cell of neuronal lineage" and "neuronal cell" include, but are not limited to, a heterogeneous population of neuronal types having singular or multiple transmitters and/or singular or multiple functions; preferably, these are cholinergic and sensory neurons. As used herein, the phrase "cholinergic neuron" means neurons of the Central Nervous System (CNS) and Peripheral Nervous System (PNS) whose neurotransmitter is acetylcholine; exemplary are basal forebrain, striatal, and spinal cord neurons. As used herein, the phrase "sensory neuron" includes neurons responsive to environmental cues (e.g., temperature, movement) from, e.g., skin, muscle and joints; exemplary is a neuron from the dorsal root ganglion.

A "trophic factor-responsive cell," as defined herein, is a cell which includes a receptor to which a trophic factor can specifically bind; examples include neurons (e.g., cholinergic and sensory neurons) and non-neuronal cells (e.g., monocytes and neoplastic cells).

The bridged indenopyrrolocarbazole compounds described herein find utility in both research and therapeutic settings in, for example, inhibition of enzymatic activity. For example, in a research environment, the compounds can be used in the development of assays and models for further enhancement of the understanding of the roles that inhibition of serine/threonine or tyrosine protein kinase (e.g., PKC, trk tyrosine kinase) play in the mechanistic aspects of the associated disorders and diseases. In a therapeutic setting, the compounds which inhibit these enzymatic activities can be used to inhibit the deleterious consequences of these enzymes with respect to disorders such as cancer.

As the Examples below demonstrate, inhibition of enzymatic activity using the bridged indenopyrrolocarbazole compounds can be determined using, for example, the following assays:

1. trkA Tyrosine Kinase Activity inhibition assay;
2. Inhibition of NGF-stimulated trk phosphorylation in a whole cell preparation;
3. Vascular Endothelial Growth Factor Receptor(VEGFR) kinase inhibition assay;
4. PKC Activity inhibition assay; and
5. PDGFR inhibition assay.

The disclosed bridged indenopyrrolocarbazole compounds can be used to enhance the function and/or survival of cells of neuronal lineage in a mammal, e.g., a human. In these contexts, the compounds can be utilized individually or with other fused pyrrolocarbazoles and/or indolocarbazoles, or in combination with other beneficial molecules which also evidence the ability to effect the function and/or survival of a designated cell.

A variety of neurological disorders are characterized by neuronal cells which are dying, injured, functionally compromised, undergoing axonal degeneration, at risk of dying, etc. These disorders include, but are not limited to: Alzheimer's disease; motor neuron disorders (e.g. amyotrophic lateral sclerosis); Parkinson's disease; cerebrovascular disorders (e.g., stroke, ischaemia); Huntington's disease; AIDS dementia; epilepsy; multiple sclerosis; peripheral neuropathies (e.g., those affecting DRG neurons in chemotherapy-associated peripheral neuropathy) including diabetic neuropathy; disorders induced by excitatory amino acids; and disorders associated with concussive or penetrating injuries of the brain or spinal cord.

ChAT catalyzes the synthesis of the neurotransmitter acetylcholine, and it is considered an enzymatic marker for a functional cholinergic neuron. A functional neuron is also capable of survival. Neuron survival is assayed by quantitation of the specific uptake and enzymatic conversion of a dye (e.g., calcein AM) by living neurons.

Because of their varied utilities, the bridged indenopyrrolocarbazole compounds disclosed herein find utility in a variety of settings. The compounds can be used in the development of in vitro models of neuronal cell survival, function, identification, or for the screening of other synthetic compounds which have activities similar to that of the bridged indenopyrrolocarbazole compounds. The compounds can be utilized in a research environment to investigate, define and determine molecular targets associated with functional responses. For example, by radiolabelling a bridged indenopyrrolocarbazole compound associated with a specific cellular function (e.g., mitogenesis), the target entity to which the derivative binds can be identified, isolated, and purified for characterization.

The compounds are useful, inter alia, not only for enhancing trophic factor-induced activities of trophic responsive cells, e.g., cholinergic neurons, but also may function as survival promoting agents for other neuronal cell types, e.g., dopaminergic or glutamatergic. Growth factor may regulate survival of neurons by signaling cascades downstream of the small GTP binding proteins ras, rac, and cdc42(Denhardt, D. T., Biochem. J., 1996, 318, 729). Specifically, activation of ras leads to phosphorylation and activation of extracellular receptor-activated kinase (ERK), which has been linked to biological growth and differentiation processes. Stimulation of rac/cdc42 leads to an increase in activation of JNK and p38, responses that are associated with stress, apoptosis, and inflammation. Although growth factor responses are primarily via the ERK pathway, affecting these latter processes may lead to alternative mechanisms of neuronal survival which may mimic growth factor enhancing survival properties (Xia et al., Science, 1995, 270, 1326). The compounds may also function as survival promoting agents for neuronal and non-neuronal cells by mechanisms related to, but also distinct from, growth factor mediated survival, for example, inhibition of the JNK and p38 MAPK pathways which may lead to survival by inhibition of apoptotic cell death processes.

The present compounds are useful in the treatment of disorders associated with decreased ChAT activity or the death, injury to spinal cord motoneurons, and also have utility in, for example, diseases associated with apoptotic cell death of the central and peripheral nervous system, immune system and in inflammatory diseases.

The bridged indenopyrrolocarbazole compounds described herein may also find utility in the treatment of disease states involving malignant cell proliferation, such as many cancers.

The pharmaceutically acceptable salts of Compounds (I) include pharmaceutically acceptable acid addition salts, metal salts, ammonium salts, organic amine addition salts, and amino acid addition salts. Examples of the acid addition salts are inorganic acid addition salts such as hydrochloride, sulfate and phosphate, and organic acid addition salts such as acetate, maleate, fumarate, tartrate, citrate and lactate; examples of the metal salts are alkali metal salts such as lithium salt, sodium salt and potassium salt, alkaline earth metal salts such as magnesium salt and calcium salt, aluminum salt, and zinc salt; examples of the ammonium salts are ammonium salt and tetramethylammonium salt; examples of the organic amine addition salts are salts with morpholine and piperidine; and examples of the amino acid addition salts are salts with glycine, phenylalanine, glutamic acid and lysine.

Compounds provided herein can be formulated into pharmaceutical compositions by admixture with pharmaceutically acceptable nontoxic excipients and carriers. Such compositions can be prepared for use in parenteral administration, particularly in the form of liquid solutions or suspensions; or oral administration, particularly in the form of tablets or capsules; or intranasally, particularly in the form of powders, nasal drops, or aerosols; or dermally, via, for example, trans-dermal patches.

The composition can be conveniently administered in unit dosage form and may be prepared by any of the methods well known in the pharmaceutical art, for example, as described in *Remington's Pharmaceutical Sciences* (Mack Pub. Co., Easton, Pa., 1980). Formulations for parenteral administration may contain as common excipients sterile water or saline, polyalkylene glycols such as polyethylene glycol, oils and vegetable origin, hydrogenated naphthalenes and the like. In particular, biocompatible, biodegradable lactide polymer, lactide/glycolide copolymer, or polyoxyethylene-polyoxypropylene copolymers may be useful excipients to control the release of the active compounds. Other potentially useful parenteral delivery systems for these active compounds include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, a salicylate for rectal administration, or citric acid for vaginal administration. Formulations for trans-dermal patches are preferably lipophilic emulsions.

The compounds of this invention can be employed as the sole active agent in a pharmaceutical composition. Alternatively, they can be used in combination with other active ingredients, e.g., other growth factors which facilitate neuronal survival or axonal regeneration in diseases or disorders.

Compound of Formula I and pharmaceutically acceptable salts thereof can be administered orally or non-orally, e.g., as an ointment or an injection. The concentrations of the compounds of this invention in a therapeutic composition can vary. The concentration will depend upon factors such as the total dosage of the drug to be administered, the chemical characteristics (e.g., hydrophobicity) of the compounds employed, the route of administration, the age, body weight and symptoms of a patient, etc. The compounds of this invention typically are provided in an aqueous physiological buffer solution containing about 0.1 to 10% w/v compound for parenteral administration. Typical dose ranges are from about 1 $\mu$g/kg to about 1 g/kg of body weight per day; a preferred dose range is from about 0.01 mg/kg to 100 mg/kg of body weight per day, and preferably about 0.1 to 20 mg/kg once to four times per day. A preferred dosage of drug to be administered is likely to depend on variables such as the type and extent of progression of the disease or disorder, the overall health status of the particular patient, the relative biological efficacy of the compound selected, and formulation of the compound excipient, and its route of administration.

Compounds of Formula I and pharmaceutically acceptable salts thereof can be administered alone, or in the form of various pharmaceutical compositions, according to the pharmacological activity and the purpose of administration. The pharmaceutical compositions in accordance with the present invention can be prepared by uniformly mixing an effective amount of a compound of Formula I or a pharmaceutically acceptable salt thereof, as an active ingredient, with a pharmaceutically acceptable carrier. The carrier may take a wide range of forms according to the forms of composition suitable for administration. It is desired that such pharmaceutical compositions are prepared in a unit dose form suitable for oral or non-oral administration. The forms for non-oral administration include ointment and injection.

Tablets can be prepared using excipients such as lactose, glucose, sucrose, mannitol and methyl cellulose, disintegrating agents such as starch, sodium alginate, calcium carboxymethyl cellulose and crystalline cellulose, lubricants such as magnesium stearate and talc, binders such as gelatin, polyvinyl alcohol, polyvinyl pyrrolidone, hydroxypropyl cellulose and methyl cellulose, surfactants such as sucrose fatty acid ester and sorbitol fatty acid ester, and the like in a conventional manner. It is preferred that each tablet contains 15–300 mg of the active ingredient.

Granules can be prepared using excipients such as lactose and sucrose, disintegrating agents such as starch, binders such as gelatin, and the like in a conventional manner. Powders can be prepared using excipients such as lactose and mannitol, and the like in a conventional manner. Capsules can be prepared using gelatin, water, sucrose, gum arabic, sorbitol, glycerin, crystalline cellulose, magnesium stearate, talc, and the like in a conventional manner. It is preferred that each capsule contains 15–300 mg of the active ingredient.

Syrup preparations can be prepared using sugars such as sucrose, water, ethanol, and the like in a conventional manner.

Ointment can be prepared using ointment bases such as vaseline, liquid paraffin, lanolin and macrogol, emulsifiers such as sodium lauryl lactate, benzalkonium chloride, sorbitan mono-fatty acid ester, sodium carboxymethyl cellulose and gum arabic, and the like in a conventional manner.

Injectable preparations can be prepared using solvents such as water, physiological saline, vegetable oils (e.g., olive oil and peanut oil), ethyl oleate and propylene glycol, solubilizing agents such as sodium benzoate, sodium salicylate and urethane, isotonicity agents such as sodium chloride and glucose, preservatives such as phenol, cresol, p-hydroxybenzoic ester and chlorobutanol, antioxidants such as ascorbic acid and sodium pyrosulfite, and the like in a conventional manner.

The invention is further illustrated by way of the following examples which are intended to elucidate the invention. These examples are not intended, nor are they to be construed, as limiting the scope of the disclosure.

EXAMPLES

Example 1

Inhibition of trkA Tyrosine Kinase Activity

Selected bridged indenopyrrolocarbazole compounds were tested for their ability to inhibit the kinase activity of baculovirus-expressed human trka cytoplasmic domain using an ELISA-based assay as previously described (Angeles et al., *Anal. Biochem.* 236: 49–55, 1996). Briefly, the 96-well microtiter plate was coated with substrate solution (recombinant human phospholipase C-$\gamma$l/glutathione S-transferase fusion protein (Rotin et al., *EMBO J.,* 11: 559–567, 1992). Inhibition studies were performed in 100 $\mu$l assay mixtures containing 50 mM Hepes, pH 7.4, 40 $\mu$M ATP, 10 mM MnCl$_2$, 0.1% BSA, 2% DMSO, and various concentrations of inhibitor. The reaction was initiated by addition of trkA kinase and allowed to proceed for 15 minutes at 37° C. An antibody to phosphotyrosine (UBI) was then added, followed by a secondary enzyme-conjugated antibody, alkaline phosphatase-labelled goat anti-mouse IgG (Bio-Rad). The activity of the bound enzyme was measured via an amplified detection system (Gibco-BRL). Inhibition data were analyzed using the sigmoidal dose-response (variable slope) equation in GraphPad Prism. The concentration that resulted in 50% inhibition of kinase activity is referred to as "$IC_{50}$". Results are summarized in Table 2.

TABLE 2

Inhibitory Effects of Bridged Indenopyrrolocarbazole Compounds on trkA Kinase Activity

| Compound No. | trkA (% inh @ 300 nM) $IC_{50}$, nM |
|---|---|
| II-1 | 13 |
| II-2 | (20) |
| II-3 | 9 |
| II-4a | 76 |
| II-4b | 16 |
| II-5 | 72 |
| II-6 | 6 |
| II-7a | 11 |
| II-7b | 5 |
| II-8 | 254 |
| II-9 | (34) |
| II-10 | (17) |
| II-11 | 121 |
| II-12 | 17 |
| II-14a | 14 |
| II-14b | 242 |

Example 2
Inhibition of NGF-stimulated trk Phosphorylation in a Whole Cell Preparation The inhibition of NGF-stimulated phosphorylation of trk by selected bridged indenopyrrolocarbazole compounds was performed using a modified procedure, as described below, from that previously described (see U.S. Pat. No. 5,516, 771). NIH3T3 cells transfected with trkA were grown in 100 mm dishes. Subconfluent cells were serum-starved by replacing media with serum-free 0.05% BSA-DMEM containing compound (100 nM and 1 μM) or DMSO (added to controls) for one hour at 37° C. NGF (Harlan/Bioproducts for Science) was then added to the cells at a concentration of 10 ng/ml for 5 minutes. Cells were lysed in buffer containing detergent and protease inhibitors. Clarified cell lysates were normalized to protein using BCA method and immunoprecipitated with anti-trk antibody. Polyclonal anti-trk antibody was prepared against a peptide corresponding to the 14 amino acids at the carboxy terminus of trk (Martin-Zanca et al., *Mol. Cell. Biol.* 9: 24–33, 1989). The immune complexes were collected on Protein A Sepharose beads (Sigma Chem. Co., St. Lois, Mo.), separated by SDS polyacrylamide gel electrophoresis (SDS-PAGE), and transferred to a polyvinylidene difluoride (PVDF) membrane. The membrane was immunoblotted with anti-phosphotyrosine antibody (UBI), followed by incubation with horseradish peroxidase coupled goat anti-mouse IgG (Bio-Rad Laboratories, Hercules, Calif.). Phosphorylated proteins were visualized using ECL (Amersham Lite Science, Inc., Arlington Heights, Ill.). The area of the trk protein band was measured and compared to NGF-stimulated control. The inhibition scoring system used, based on percent decrease in trk protein band, was as follows: 0=no decrease; 1=1–25%; 2=26–49%; 3=50–75%; 4=76–100% Results are shown below in Table 3.

TABLE 3

Effects of Bridged Indenopyrrolocarbazole Compounds on NGF-stimulated trkA Phosphorylation in NIH3T3 Cells

| Compound No. | Inhibition Score | |
|---|---|---|
| | at 100 nM | at 1000 nM |
| II-1 | 3 | 4 |
| II-3 | 1 | 4 |
| II-4b | 0 | 2 |
| II-6 | 4 | 4 |
| II-7a | 3 | 4 |
| II-7b | 3 | 4 |

Example 3
Inhibition of Vascular Endothelial Growth Factor Receptor Kinase Activity Bridged indenopyrrolocarbazole compounds were examined for their inhibitory effects on the kinase activity of baculovirus-expressed VEGF receptor (human flk-1, KDR, VEGFR2) kinase domain using the procedure described for the trkA kinase ELISA assay described above. The kinase reaction mixture, consisting of 50 mM Hepes, pH 7.4, 40 μM ATP, 10 mM $MnCl_2$, 0.1% BSA, 2% DMSO, and various concentrations of inhibitor, was transferred to PLC-γ/GST-coated plates. VEGFR kinase was added and the reaction was allowed to proceed for 15 min. at 37° C. Detection of phosphorylated product was accomplished by addition of anti-phosphotyrosine antibody (UBI). A secondary enzyme-conjugated antibody was delivered to capture the antibody-phosphorylated PLC-γ/GST complex. The activity of the bound enzyme was measured via an amplified detection system (Gibco-BRL). Inhibition data were analyzed using the sigmoidal dose-response (variable slope) equation in GraphPad Prism. Results are summarized in Table 4.

TABLE 4

Inhibitory Effects of Bridged Indenopyrrolocarbazole Compounds on VEGF Receptor Kinase Activity

| Compound No. | VEGFR kinase (% Inh. @ 300 nM) $IC_{50}$, nM |
|---|---|
| II-1 | 30 |
| II-1b | 67 |
| II-2 | >10,000 |
| II-3 | 71 |
| II-4a | 17 |
| II-4b | 184 |
| II-5 | 398 |
| II-6 | 9 |
| II-7a | 87 |
| II-7b | 260 |
| II-8 | 26 |
| II-9 | 318 |
| II-10 | 601 |
| II-11 | 205 |
| II-12 | 20 |
| II-13 | 8 |
| II-14a | 32 |
| II-14b | 538 |
| II-15 | 25 |
| II-16a | 43 |
| II-16b | 57 |

Example 4
Inhibition of Protein Kinase C Activity

Protein kinase C activity was assessed using the Millipore Multiscreen TCA "in-plate" assay as described in Pitt, A. M.

and Lee, C. (*J. Biomol. Screening*, 1: 47–51, 1996). Assays were performed in 96-well Multiscreen-DP plates (Millipore). Each 40-ml assay mixture contained 20 mM Hepes, pH 7.4, 10 mM $MgCl_2$, 2.5 mM EGTA, 2.5 mM $CaCl_2$, 80 mg/ml phosphatidyl serine, 3.2 mg/ml diolein, 200 mg/ml histone H-1(Fluka), 5 mM [$\gamma$-$^{32}$P]ATP, 1.5 ng protein kinase C (UBI; mixed isozymes of a, b, g), 0.1% BSA, 2% DMSO, and test bridged fused pyrrolocarbazole compound. The reaction was allowed to proceed for 10 min at 37° C., then quenched by adding ice cold 50% trichloroacetic acid. The plates were allowed to equilibrate for 30 min at 4° C., then washed with ice cold 25% TCA. Scintillation cocktail was added to the plates, and the radioactivity was determined using Wallac MicroBeta 1450 PLUS scintillation counter. The $IC_{50}$ values were calculated by fitting the data to the sigmoidal dose-response (variable slope) equation in GraphPad Prism. The results are summarized in Table 5.

TABLE 5

Inhibitory Effects of Bridged Indenopyrrolocarbazole Compounds on Protein Kinase C Activity

| Compound No. | PKC (% Inh. @ 1 uM) $IC_{50}$, nM |
|---|---|
| II-1 | 1300 |
| II-2 | (−9) |
| II-3 | (23) |
| II-4a | (18) |
| II-4b | (28) |
| II-5 | (37) |
| II-6 | 221 |
| II-7a | 696 |
| II-7b | 568 |
| II-8 | 1078 |
| II-9 | (5) |
| II-10 | (5) |
| II-11 | (19) |
| II-12 | 518 |
| II-13 | 576 |
| II-14a | 126 |
| II-14b | 1239 |
| II-15 | (02) |
| II-16a | 46 |

Example 5
Inhibition of Platelet Derived Growth Factor Receptor Kinase Activity

Bridged indenopyrrolocarbazole compounds were examined for their inhibitory effects on the kinase activity of baculovirus-expresses PDGFβ receptor kinase domain using the trkA kinase ELISA described above. Assays were performed in substrate (PLC-γ/GST)-coated 96-well microtiter plates. Each 100-μl reaction mixture contained 50 mM HEPES, pH 7.4, 20 μM ATP, 10 mM $MnCl_2$, 0.1% BSA, 2% DMSO, and various concentrations of inhibitor. The reaction was initiated by addition of prephosphorylated recombinant human enzyme (10 ng/ml PDGFRβ) and allowed to proceed for 15 minutes at 37° C. The prephosphorylated enzyme was prepared prior to use by incubation of the kinase in buffer containing 20 μM ATP and 10 mM $MnCl_2$ for 1 hour at 4° C. Detection of phosphorylated product was done by adding horseradish peroxidase (HRP)-conjugated anti-phosphotyrosine antibody (UBI). The HRP substrate solution containing 3, 3'-5, 5'-tetramethylbenzidine and hydrogen peroxide was later added and the plates were incubated for 10 minutes at room temperature. The reaction was quenched with acid and the resulting absorbance was read at 450 nm using a Microplate Bio-kinetics Reader (Bio-Tek Instrument EL 312e). Inhibition data were analyzed using the sigmoidal dose-response (variable slope) equation in GraphPad Prism. The results are summarized in Table 6.

TABLE 6

PDGFR Inhibitory Effects of Bridged Indenopyrrolocarbazole Compounds

| Compound No. | PDGFR (% Inh. @ 1 μM) $IC_{50}$, nM |
|---|---|
| II-1 | 1383 |
| II-2 | (7) |
| II-3 | (28) |
| II-4a | (0) |
| II-4b | (17) |
| II-5 | 1076 |
| II-6 | 96 |
| II-7a | (36) |
| II-7b | (34) |
| II-8 | (15) |
| II-9 | (24) |
| II-10 | (23) |
| II-11 | (15) |
| II-12 | 125 |
| II-13 | 1229 |
| II-14a | 81 |
| II-14b | 1406 |

Example 6
Enhancement of Spinal Cord ChAT Activity

As discussed above, ChAT is a specific biochemical marker for functional cholinergic neurons. Cholinergic neurons represent a major cholinergic input into the hippocampal formation, olfactory nucleus, interpeduncular nucleus, cortex, amygdala, and parts of the thalamus. In the spinal cord, the motor neurons are cholinergic neurons which contain ChAT (Phelps et al., *J. Comp. Neurol.* 273:459–472 (1988) ). ChAT activity has been used to study the effects of neurotrophins (e.g., NGF or NT-3) on the survival and/or function of cholinergic neurons. The ChAT assay also serves as an indication of the regulation of ChAT levels within cholinergic neurons.

Bridged indenopyrrolocarbazole compounds increased ChAT activity in the dissociated rat embryonic spinal cord culture assay (Table 7). For example, In these assays, a compound was directly added to a dissociated spinal cord culture. Compounds which increased ChAT activity at least 120% of the control activity were considered active. Results are summarized in Table 7.

TABLE 7

Enhancement of Spinal Cord ChAT Activity by Bridged Indenopyrrolocarbazole Compounds
Spinal Cord ChAT
% control

| Compound No. | Activity at 30 nM | Maximal Activity |
|---|---|---|
| II-1 | 114 | 139 @ 300 nM |

Methods: Fetal rat spinal cord cells were dissociated, and experiments were performed as described (Smith et al., *J. Cell Biology* 101:1608–1621(1985); Glicksman et al., *J. Neurochem.* 61:210–221(1993) ). Dissociated cells were prepared from spinal cords dissected from rats (embryonic day 14–15) by standard trypsin dissociation techniques (Smith et al., supra.). Cells were plated at 6×10$^5$ cells/cm$^2$ on poly-1-ornithine coated plastic tissue culture wells in serum-free N2 medium supplemented with 0.05% bovine serum albumin (BSA) (Bottenstein et al., *PNAS USA* 76:514–517 (1979) ). Cultures were incubated at 37° C. in a humidified atmosphere of 5% $CO_2$/95% air for 48 hours. ChAT activity was measured after 2 days in vitro using a modification of the Fonnum procedure (Fonnum, *J. Neurochem.* 24:407–409 (1975) ) according to McManaman et al. and Glicksman et al. (McManaman et al., *Developmental Biology* 125:311–320(1988); Glicksman et al., *J. Neurochem.*, supra.).

Compounds of Formula II described in the examples are listed in Table 8. Values for $R^1$, $R^4$, $R^6$, and $R^7$ are H; Y is O; and n is 1.

with a bi-functional reagent (V) results in an electrophilic addition to the C=Y bond of (V) leading to the initial intermediate (VI)/(X). Treatment of intermediate(s) (VI)(X) and/or (VII)/(XI) with either a sulphonic acid or a Lewis acid, e.g. boron trifluoride etherate, provides the bridged indenopyrrolocarbazoles (I)/(II).

The lactam nitrogen protection strategy (shown in FIGS. 3 and 4) can be carried out by either an acid or a base-catalyzed process. The acid-catalyzed reaction can be carried out with a resin-bound reagent allowing immobilization of the indenopyrrolocarbazole (III)/(VIII) to a polymeric support, such as a polystyrene-based, Rink acid resin (XII) (FIG. 3), providing (XIII). Alternatively, the acid-catalyzed

TABLE 8

II

| Compound No. | $A_1A_2$ | $B_1B_2$ | $R_2$ | $R_3$ | $R_5$ | $R_8$ | Z | m |
|---|---|---|---|---|---|---|---|---|
| II-1 | H,H | O | H | H | H | H | bond | 1 |
| II-1b | H,H | O | H | H | H | H | bond | 1 |
| II-2 | H,H | O | Et | H | H | H | bond | 1 |
| II-3 | H,H | O | H | H | H | Me | bond | 1 |
| II-4a | H,H | O | H | H | H | Me | bond | 2 |
| II-4b | H,H | O | H | H | H | Me | bond | 2 |
| II-5 | H,H | O | H | 3-Br | H | Me | bond | 1 |
| II-6 | H,H | O | H | H | 10-OMe | H | bond | 1 |
| II-7a | H,H | O | H | H | H | Me | O | 1 |
| II-7b | H,H | O | H | H | H | Me | O | 1 |
| II-8 | O | H,H | H | H | H | H | bond | 1 |
| II-9 | H,H | O | H | 3-(3'-$NH_2$—Ph) | H | H | bond | 1 |
| II-10 | O | O | OH | H | H | H | bond | 1 |
| II-11 | H,H | O | H | H | H | $CO_2$—Et | bond | 1 |
| II-12 | H,H | O | H | H | H | $CH_2$—OH | bond | 1 |
| II-13 | H,H | O | H | H | 9-OMe | H | bond | 1 |
| II-14a | H,H | O | H | H | H | H | bond | 1 |
| II-14b | H,H | O | H | H | H | H | bond | 1 |
| II-15 | H,H | O | H | 3-$CH_2$O—$CH_2$OEt | H | H | bond | 1 |
| II-16a | H,H | O | H | H | H | H | O | 1 |
| II-16b | H,H | O | H | H | H | H | O | 1 |

General Description of the Synthetic Processes and Examples

Figure 2:
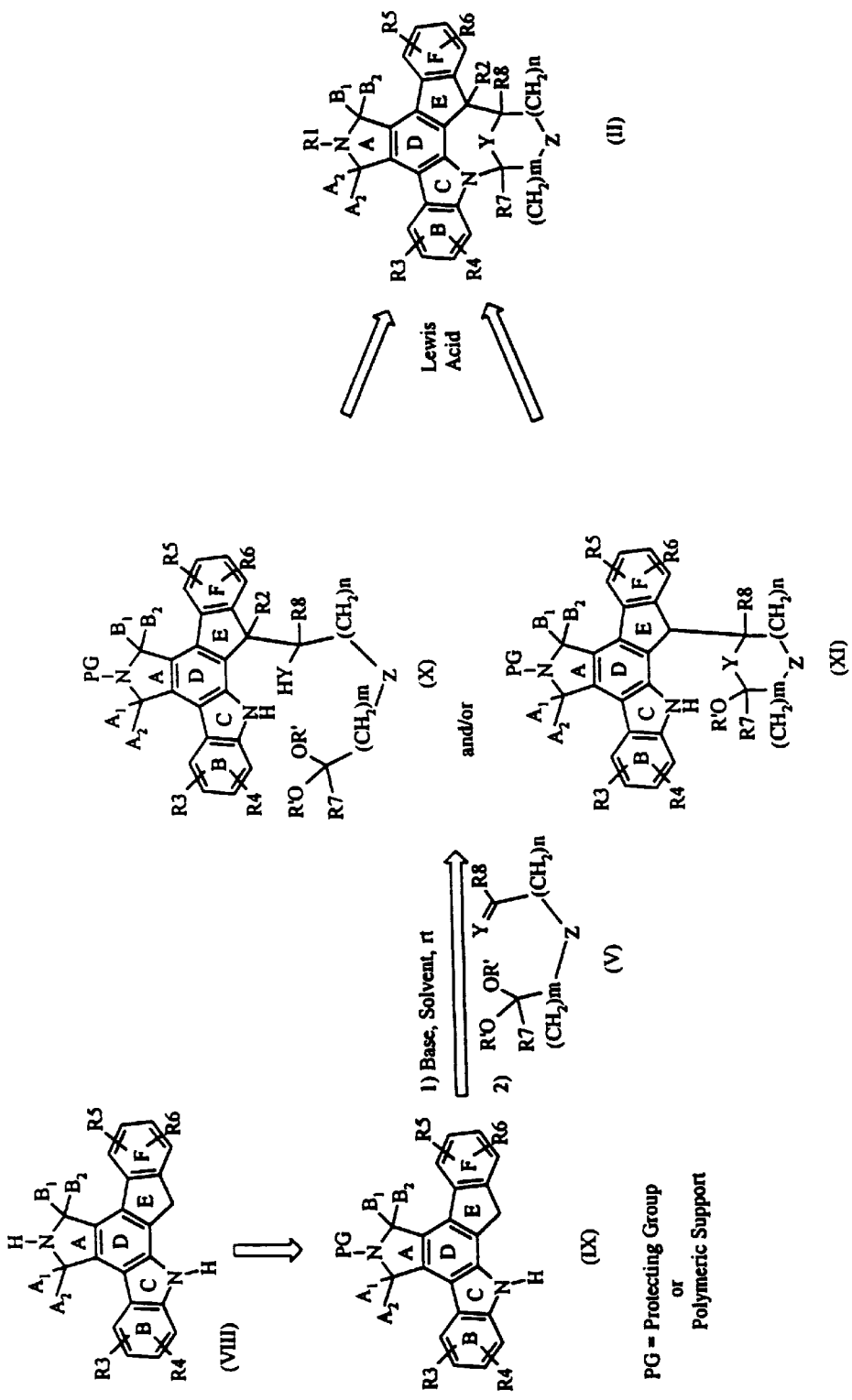
FIG. 2 is a schematic drawing showing a general preparation of bridged indenopyrrolocarbazoles.
Figure 4:
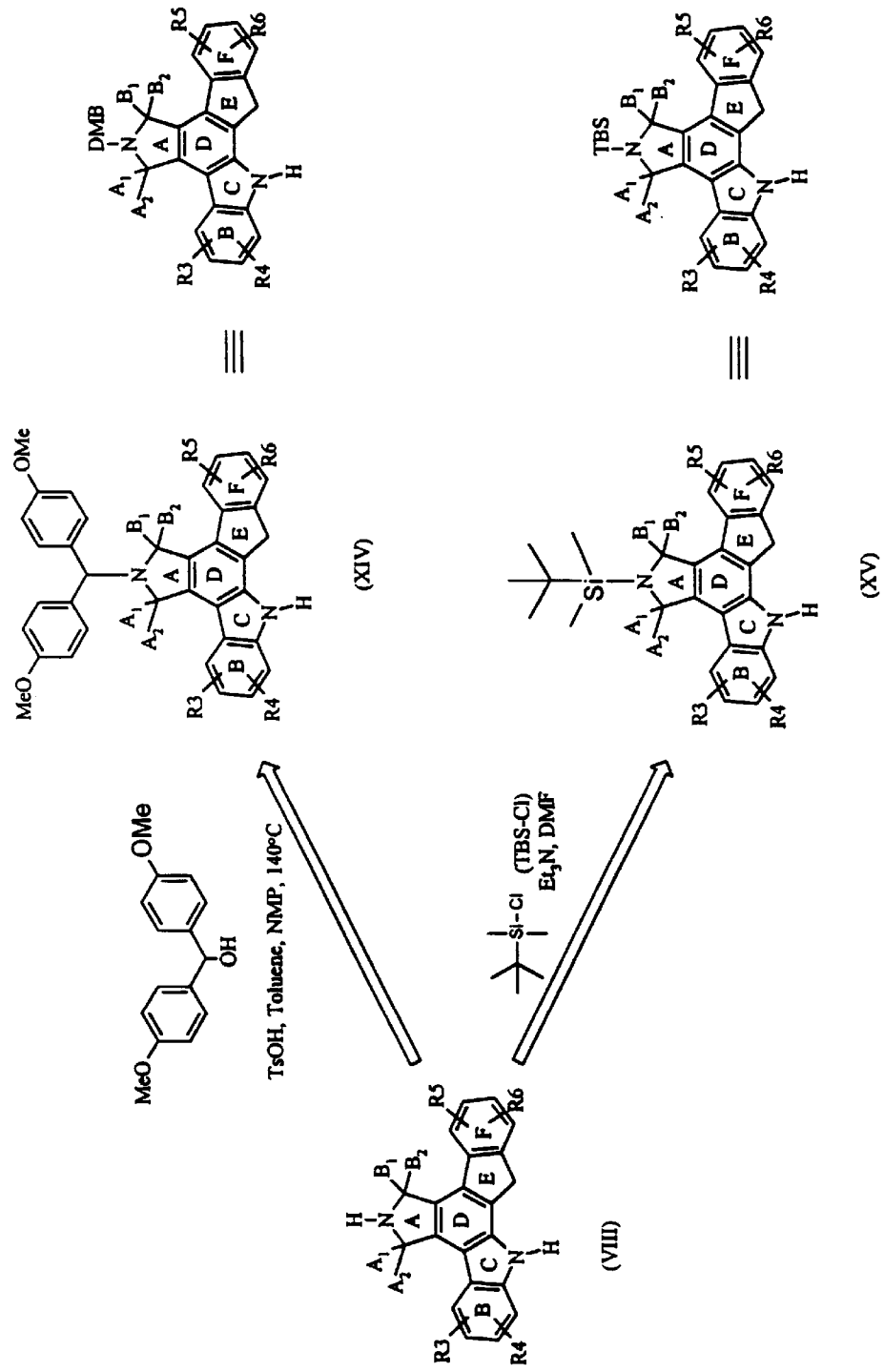
FIG. 4 is a schematic drawing showing the preparation of protected, soluble indenopyrrolocarbazoles.

The general synthetic route employed to prepare the bridged indenopyrrolocarbazoles of this invention is shown in FIGS. 1 and 2. The general procedures for synthesis of the indenopyrrolocarbazoles (III)/(VIII) can be performed as described in U.S. Pat. No. 5,705,511, the disclosure of which is hereby incorporated by reference in its entirety. When $R^1$ is H, the lactam nitrogen of the indenopyrrolo-carbazoles (III)/(VIII) is protected with an appropriate protecting group leading to (IV)/(IX). The protected compounds are treated with an appropriate base in anhydrous organic solvent(s), which results in the generation of a dark red solution which is believed to be the carbanion. Reaction of the carbanion reaction can be carried out with a soluble reagent to yield a compound (XIV) (FIG. 4). The silyl-protected compound (XV) is produced under base catalysis (FIG. 4).

Figure 5:
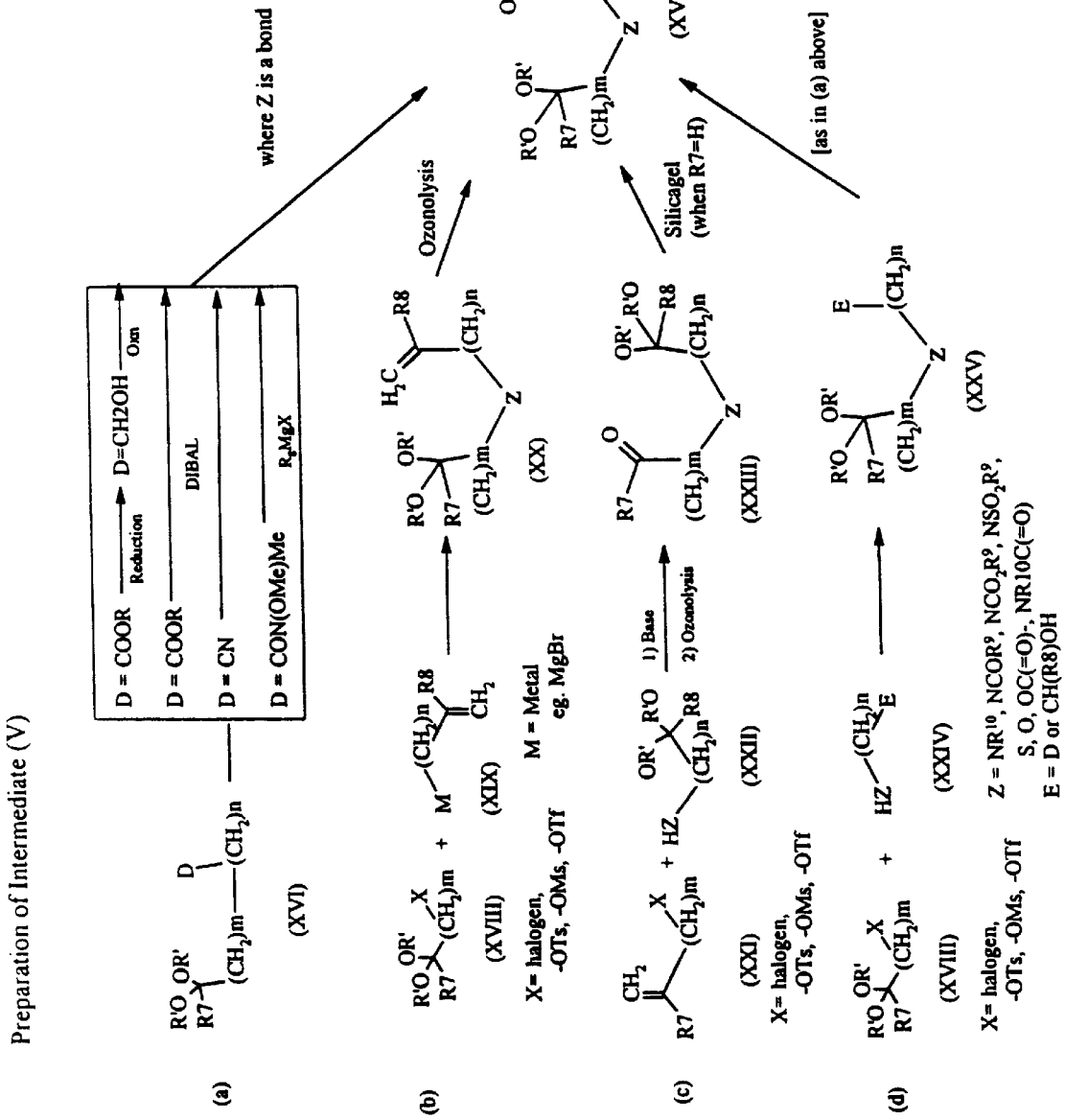
FIG. 5 is a schematic drawing showing the preparation of intermediate V.

FIG. 5 describes several methods for preparing intermediate (V). Procedure (a) describes the transformations of various acetals (XVI) to (XVII, Z=bond). For example, ester-acetal/ketal (XVI, D=COOR) is completely reduced to the corresponding alcohol and subsequently oxidized (e.g., Swern or Dess-Martin oxidation) to the aldehyde-acetal/ketal (XVII, $R^8$=H). Alternatively, ester-acetal/ketal (XVI, D=COOR) is partially reduced with DIBAL to afford aldehyde (XVII, $R^8$=H) directly. Similarly, reduction of nitrile-acetal (XVI, D=CN) with DIBAL gives aldehyde (XVII, R⁸=H). Keto-acetals/ketal are prepared by addition of Grignard reagents to Weinreb amide-acetal/ketal (XVI, D=CON(OMe) Me).

Intermediate (XVII, Z=bond) can also be obtained by a two step procedure outlined in Procedure (b). Addition of organometallic reagent (XIX) to acetal/ketal (XVIII) gives alkene (XX) which upon ozonolysis followed by a reductive workup affords keto-acetal/ketal (XVII). Preparation of intermediate (XVII, Z=heteroatom) by a two step procedure is outlined in Procedure (c). Coupling acetal (XXII) with alkene (XXI) followed by ozonolysis (with a reductive workup) of the resulting alkene gives keto-acetal/ketal (XVII). Alternatively, intermediate (XVII, Z=heteroatom) is prepared by a two step procedure outlined in Procedure (d). Reaction of compound (XXIV) with acetal/ketal (XVIII) gives (XXV) which is transformed to keto-acetal/ketal (XVII) by the methods described in Procedure (a). Condensation of keto-acetal/ketal (XVII) with hydroxylamines, hydrazines, N-alkyl-N-alkoxyamines, and amines gives intermediate (XXVI) bearing an electrophilic C=N functionality.

Figure 6:
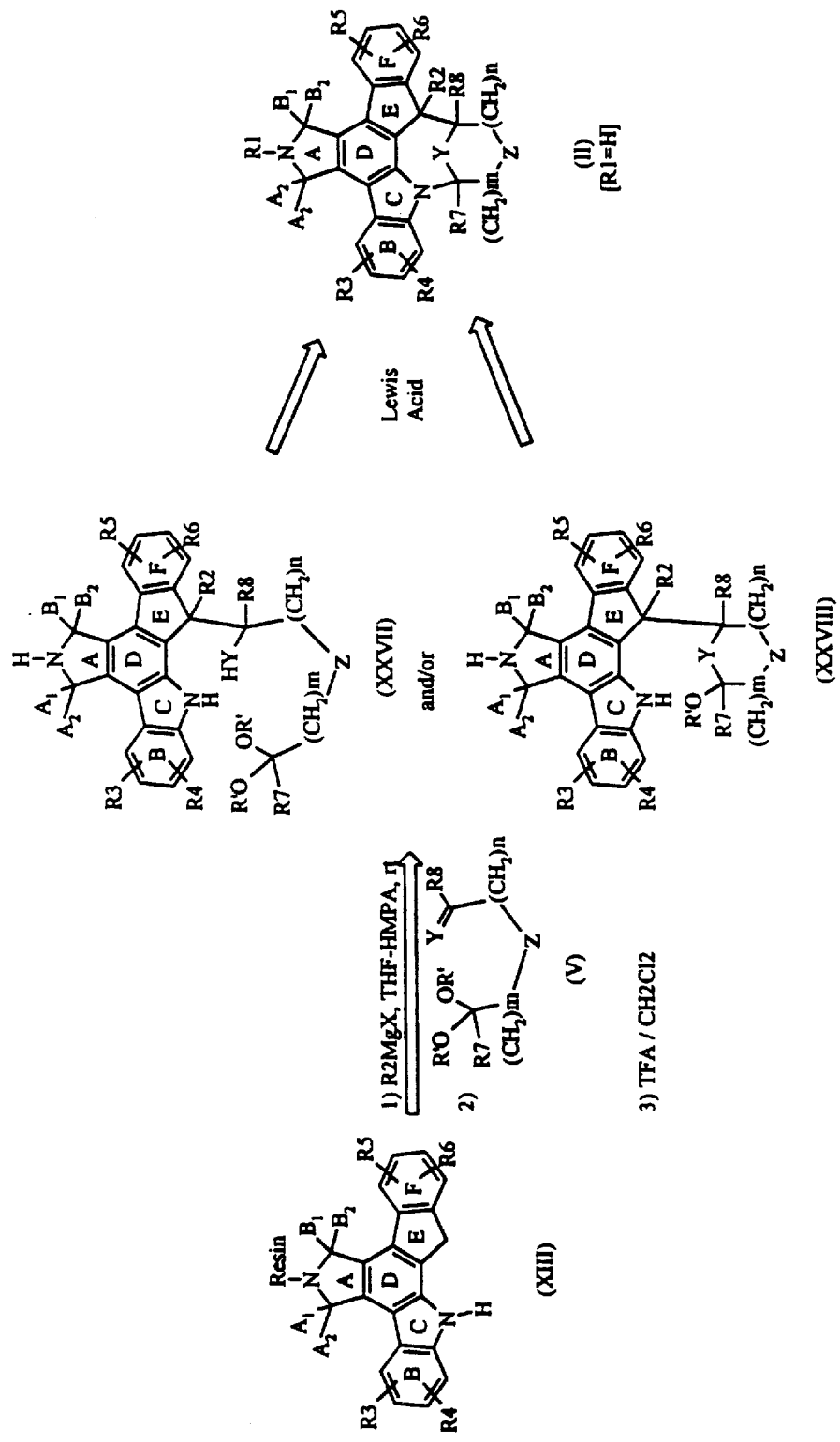
FIG. 6 is a schematic drawing showing the preparation of bridged indenopyrrolocarbazoles using method A.

The resin-bound indenopyrrolocarbazole (XIII) [FIG. 6, Method A] is treated with an excess of a Grignard reagent as a base, which results in the generation of a dark red solution of the carbanion. Subsequent reaction with (V) leads to products derived form electrophilic addition to the C=Y group. Aqueous workup and cleavage of the product(s) with dilute acid (1% TFA in methylene chloride) from the resin result in isolation of compound(s) (XXVII) and/or (XXVIII). Treatment of intermediate(s) (XXVII) and/or (XXVIII) with either a sulphonic acid or a Lewis acid, e.g. boron trifluoride etherate, provides the bridged indenopyrrolocarbazoles (II).

Figure 7:
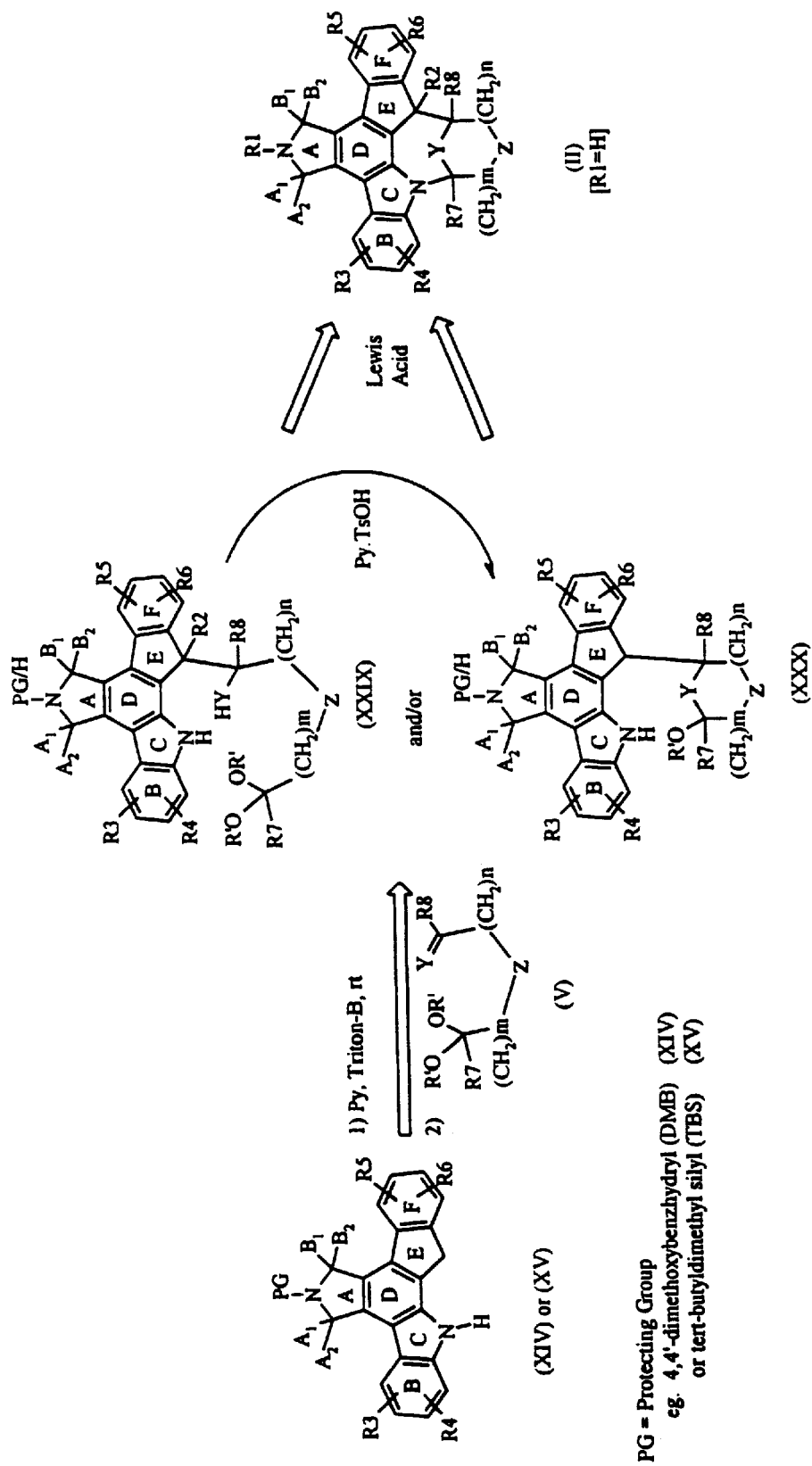
FIG. 7 is a schematic drawing showing the preparation of bridged indenopyrrolocarbazoles using method B.

A similar strategy is employed for reaction of the soluble lactam protected intermediate, e.g. (XV) (FIG. 7, Method B). However, in this case intermediate (XV) is treated with Triton B in pyridine as a base instead of the Grignard reagent. Intermediate(s) (XXIX) and/or (XXX) can be isolated with the lactam protecting group intact, which is amenable to chromatographic purification. As in method A, (FIG. 6), treatment with a Lewis acid (such as boron trifluoride etherate)provides the bridged indenopyrrolocarbazoles (II), where R¹=H.

Figure 8:
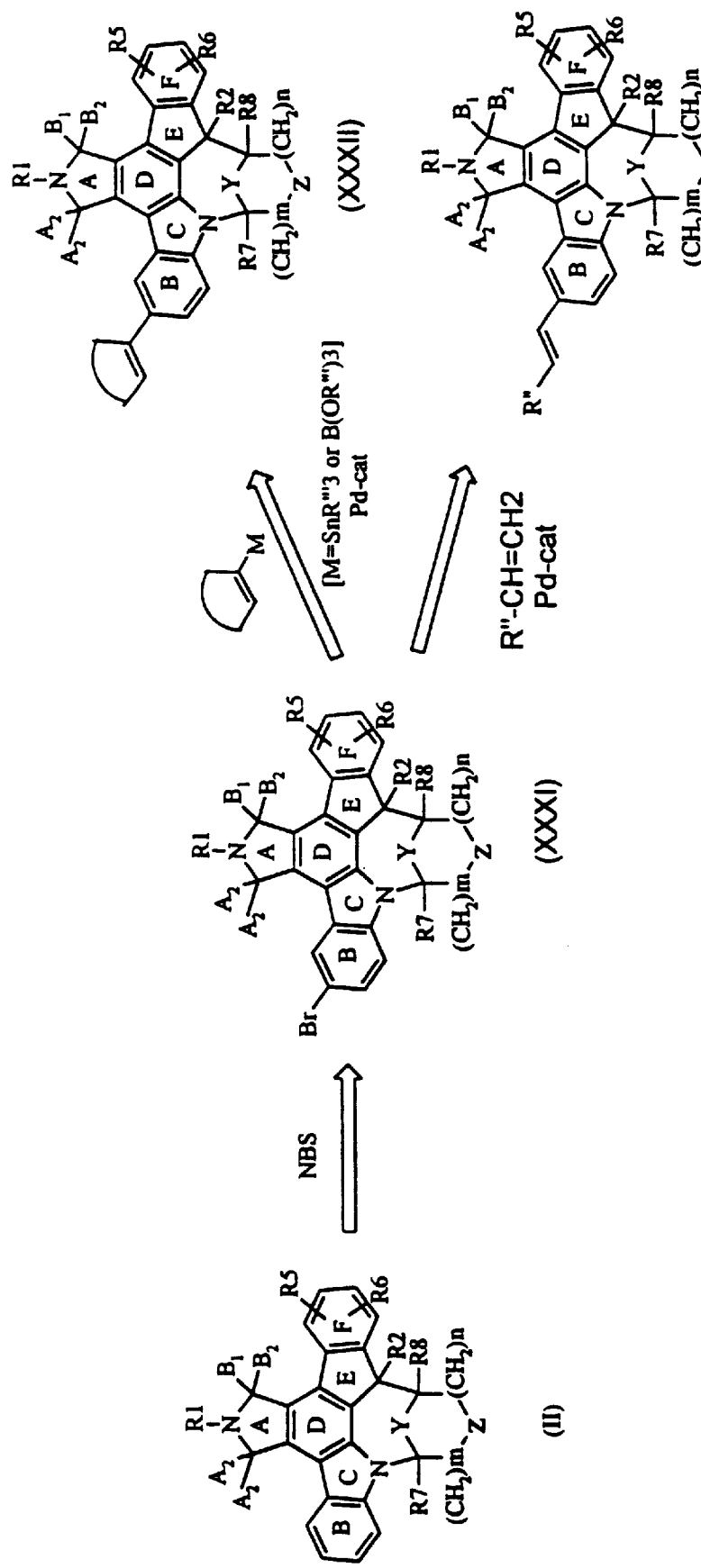
FIG. 8 is a schematic drawing showing the preparation of B ring-substituted bridged indenopyrrolocarbazoles.

The introduction of groups $R^3$, $R^4$, $R^5$ and $R^6$ can be carried out as described in U.S. Pat. Nos. 5,705,511 and 4,923,986, the disclosures of which are incorporated by reference in their entirety. An R³ substituent can otherwise be introduced after the construction of the bridged indenopyrrolocarbazoles, as shown in FIG. 8. The 3 position of the B ring is brominated with NBS providing compound (XXXI). A carbon fragment is subsequently introduced by employing palladium-catalyzed Stille, Suzuki, Heck, Kumada or Castro-Stephens reactions to provide compounds of the type (XXXII), (XXXIII), etc. In addition, compound (XXXI) can provide access to compounds where the bromine group is displaced with a heteroatom, e.g. an amine-based group by utilization of Buchwald's palladium catalyzed amination chemistry.

Figure 9:
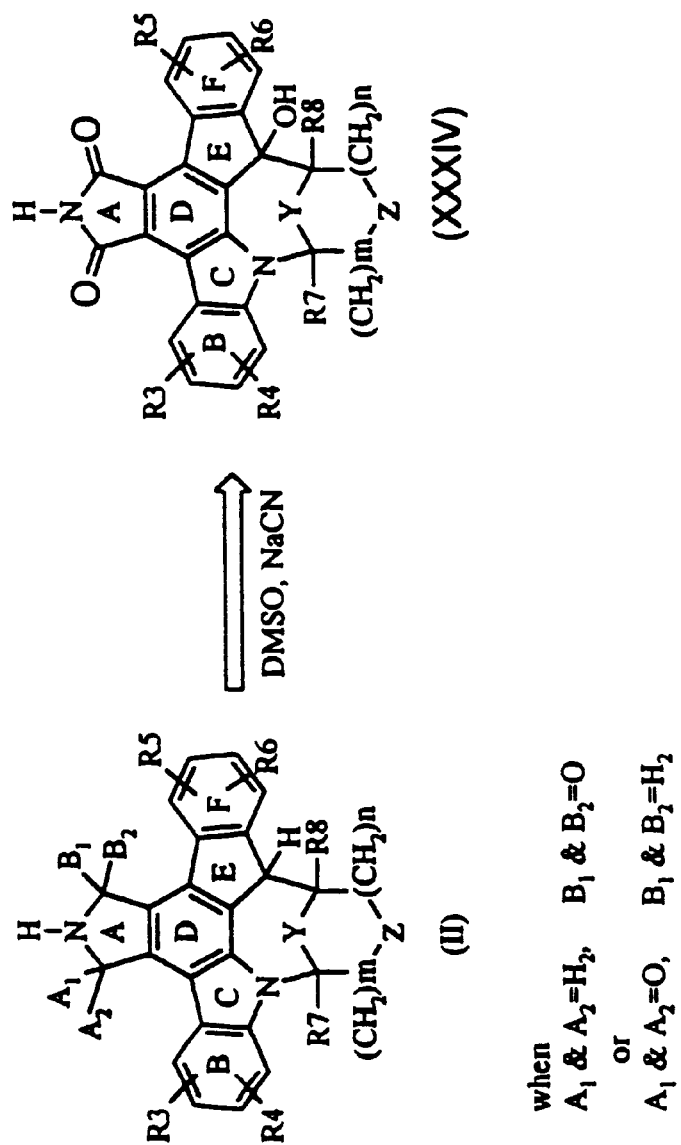
FIG. 9 is a schematic drawing showing the derivatization of the E ring of bridged indenopyrrolocarbazoles.

By an oxidative process, an oxygen linked group can be introduced at the indene carbon of the E ring, as shown in FIG. 9, compound (XXXIV). This chemistry also results in oxidation of the methylene group of the lactam (A ring) providing an imide derivative, as shown.

Figure 3:
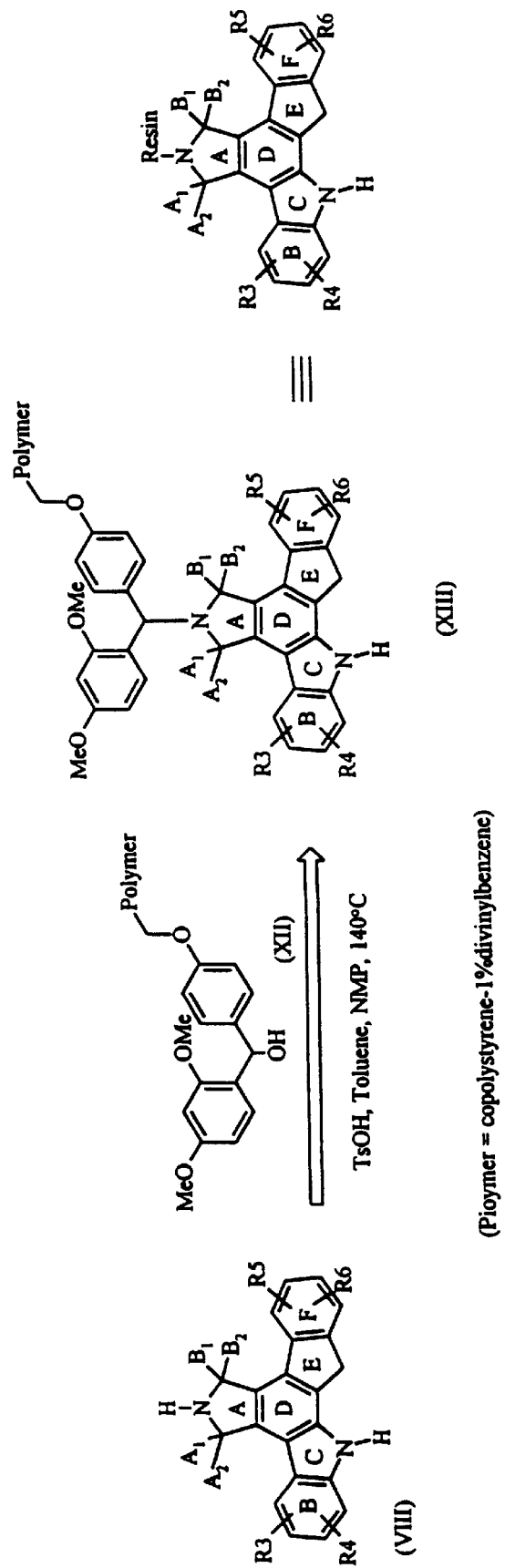
FIG. 3 is a schematic drawing showing a preparation of resin-bound indenopyrrolocarbazoles.

Example 7
Preparation of Rink Resin-bound Intermediates: (XIII-A), (XIII-B) and (XIII-C), (FIG. 3)

Example 7-A

A three neck round bottom flask fitted with an overhead mechanical stirrer and a Dean-Stark trap was sequentially charged with Rink acid resin XII (10.00 g, 0.64 mmol/g), 1-methyl-2-pyrolidinone (80 mL), benzene (350 mL), VIII-A [$A^1,A^2=H_2$, $B^1,B^2=O$, $R^3=R^4=R^5=R^6=H$)] (3.00 g) and p-toluenesulfonic acid (1.00 g). The reaction mixture was warmed to reflux for 20 hours, and then filtered. The resin was washed with THF (5×175 mL) and the filtrate set aside. The resin was then sequentially washed with DMSO (4×100 mL), 2% aqueous NaHCO₃(4×100 mL), water (4×100 mL), DMSO (2×200 mL), THF (4×100 mL) and ethyl acetate (4×100 mL). The resin was dried under vacuum (24 hours) to afford 11.70 (0.47 mmol/g) of resin bound VIII-A (XIII-A).

The original THF washings were evaporated, the residue was diluted with water (750 mL), and the resulting precipitate was filtered and sequentially washed with water, 2% aqueous NaHCO₃(4×100 mL), and water (4×100 mL). After drying under vacuum, VIII-A (1.28 g) was recovered.

Example 7-B

In a similar manner, VIII-B [$A^1,A^2=O$, $B^1,B^2=H_2$, $R^3=R^4=R^5=R^6=H$], (0.5 g) was coupled to Rink acid resin XII (1.52 g) to afford 1.58 g of resin bound VIII-B, (XIII-B).

Example 7-C

In a similar manner, VIII—C [$A^1,A^2=H_2$, $B^1,B^2=O$, $R^3=R^4=R^5=H$, $R^6=10$-OMe], (1.02 g) was coupled to Rink acid resin XII (3.12 g) to afford 3.70 (0.46 mmol/g) of resin bound compound VIII-C, (XIII-C) along with recovered compound VIII-C (0.44 g).

Example 8
Preparation of Compound (II-1), Compound (II-2), Compound (II-3), Compound (II-4a),-Compound (II-4b), Compound (II-6) and Compound (II-8). [Method A, FIG. 6]

Example 8-A

To a suspension of (XIII-A), (1.25 g) in THF (24 mL) was added a 1.0 M solution of EtMgBr (6.25 mL in THF) and the reaction was stirred for 1 hour prior to the addition of HMPA (5.0 mL). After stirring for 10 minutes, diethoxybutyraldehyde (3.0 g) [which was prepared according to the literature procedure of Paquette, L. A., Backhaus, D., Braum, R., Underiner, T. L., and Fuchs, K. *J. Am. Chem. Soc.* 1997, 119, 9662–71], was added, and the reaction was stirred for 20 hours. The reaction was quenched with 10% aqueous NH₄Cl (5 mL) and filtered. The resin was successively washed with 10% aqueous NH₄Cl (3×10 mL), water (3×10 mL), THF (3×10 mL), DMF (3×10 mL), water (3×10 mL), THF (3×10 mL), and ether (3×10 mL). The resin was dried under vacuum, taken up in methylene chloride (15 mL), and treated with trifluoroacetic acid (0.15 mL). After stirring for 1 hour, the reaction was filtered, and the filtrate was evaporated. The resulting residue was taken up in methylene chloride (20 mL) and treated with pyridinium tosylate (50 mg), and the resulting solution was stirred for 4 hours. At this time the reaction was washed with saturated aqueous NaHCO₃ and brine, and dried over MgSO₄. After filtration and solvent evaporation, the residue was purified by preparative HPLC (Zorbax RX-8, 4×25 cm, eluted with 60% MeCN/water w/0.1% trifluoroacetic acid). The appropriate fractions were neutralized with NaHCO₃ and extracted into methylene chloride (3×50 mL) and dried over MgSO₄. After filtration and solvent evaporation, 70.2 mg of compound II-1 was obtained as a white powder which had the following characteristics: ¹³C NMR (DMSO-d₆) δ171.8, 143.3, 142.4, 141.4, 140.1, 140.0, 136.6, 129.2, 127.9, 127.4, 127.1, 126.8, 124.1(2C), 122.7, 121.6, 121.5, 118.3, 112.1, 88.1, 79.2, 56.6, 45.6, 33.4, 24.8; $^1$H NMR (DMSO-d$_6$) δ9.21 (d, J=7.5, 1H), 8.62 (s, 1H), 7.98 (d, J=7.7, 1H), 7.86 (d, J=8.3, 1H), 7.71 (d, J=7.3, 1H), 7.49 (dd, J=7.9, 7.4, 1H), 7.41 (dd, J=7.5, 7.4, 1H), 7.36–7.27 (m, 2 H), 6.86 (d, J=6.0, 1H), 5.63–5.58 (m, 1H), 4.91 (s, 2H), 4.53 (d, J=3.3, 1H), 2.23–2.14 (m, 1H), 1.96–1.92 (m, 1H), 0.96–0.88 (m, 1H), 0.60–0.57 (m, 1H); MS m/z (M+H) calcd 379, obsd 379.

Also isolated by preparative HPLC of this reaction product mixture was compound II-2(0.5 mg) which had the following characteristics: $^1$H NMR (DMSO-d$_6$) δ9.17(d, J=8.1, 1H), 8.62 (s, 1H), 7.98 (d, J=7.0, 1H), 7.85 (d, J=6.8, 1H), 7.57 (d, J=6.8, 1H), 7.49 (dd, J=7.9, 7.4, 1H), 7.44–7.26 (m, 3H), 6.81 (d, J=6.0, 1H), 5.43–5.33 (m, 1H), 4.43 (s, 2H), 2.23–2.14 (m, 1H), 1.96–1.92 (m, 1H), 1.45–1.55 (m, 2H), 0.96–0.88 (m, 1H), 0.60–0.57 (m, 1H), 0.29 (t, J=7.0, 3H); MS m/z (M+H) calcd 407, obsd 407.

Example 8-B

In a similar manner, as described above for compound II-1, resin (XIII-A) (70.3 mg) was treated with 1,1-diethoxy-2-pentanone (0.75 mL) ) [which was prepared according to the literature procedure of Sworin, M. and Neuman, W. L. *J. Org. Chem.* 1988, 53, 4894–61], to afford compound II-3 (3.5 mg) which was isolated by preparative TLC (silica gel, eluted with 50% EtOAc/toluene) and had the following properties: $^1$H NMR (DMSO-d$_6$) δ9.42 (d, J=8.2, 1H), 8.58 (s, 1H), 7.95 (d, J=7.4, 1H), 7.79 (d, J=8.3, 1H), 7.71 (d, J=7.1), 7.50–7.20 (m, 4H), 6.81 (d, J=5.9, 1H), 4.90 (s, 2H), 4.46 (s, 1H), 2.35–2.20 (m, 1H), 1.98 (s, 3H), 1.75–1.60 (m, 1H), 1.25–1.00 (m, 1H), 0.35–0.15 (m, 1H); MS m/z (M+H) calcd 393, obsd 393.

Example 8-C

In a similar manner, (XIII-A) (74.3 mg) was treated with 1,1-diethoxy-2-hexanone [which was prepared according to the literature procedure of Brenner, J. E., *J. Org. Chem.* 1961, 26, 22–7] (0.75 mL) to afford compound II-4a (2.10 mg) and compound II4b (1.06 mg) which were individually isolated by preparative HPLC (Zorbax RX-8, 4×25 cm, 65% MeCN/water w/0.1% trifluoroacetic acid). Compound II-4a had the following properties: $^1$H NMR (DMSO-d$_6$) δ9.30(d, J=8.3, 1H), 8.55(s, 1H), 7.97 (d, J=7.2, 1H), 7.65 (d, J=8.5, 1H), 7.59 (d, J=7.5), 7.48 (dd, J=7.8, 7.2, 1H) 7.39–7.15 (m, 3H), 6.31 (dd, J=5.9, 5.5, 1H), 5.02 (s, 1H), 4.88 (s, 2H), 0.88 (s, 3H) other aliphatic signals lost under solvent peaks; MS m/z (M+H) calcd 407, obsd 407. Compound II-4b had the following properties: $^1$H NMR (DMSO-d$_6$) δ9.43 (d, J=8.1, 1H), 8.59 (s, 1H), 7.99 (d, J=7.3, 1H), 7.75–7.65 (m, 2H), 7.49 (dd, J=7.0, 6.4, 1H), 7.43 (dd, J=8.2, 8.1, 1H), 7.36–7.25 (m, 2H), 6.75 (s, 1H), 4.91 (s, 2H), 4.50 (s, 1H), 1.95 (s, 3H) other aliphatic signals lost under solvent peaks; MS m/z (M+H) calcd 407, obsd 407.

Example 8-D

In a similar manner, (XIII-C) (1.00 g) was treated with diethoxybutyraldehyde (3.65 g) to afford compound II-6 (87.8 mg) which was isolated by preparative HPLC (Zorbax RX-8, 2.5×25 cm, 65% MeCN/water w/0.1% trifluoroacetic acid) and had the following properties: $^1$H NMR (DMSO-d$_6$) δ9.09 (d, J=8.6, 1H), 8.60 (s, 1H), 7.95 (d, J=7.4, 1H), 7.84 (d, J=8.3, 1H), 7.47 (dd, J=7.2, 7.0, 1H), 7.35 (s, 1H), 7.29 (dd, J=7.0, 7.0, 1H), 6.98 (dd, J=8.6, 1.9, 1H), 6.83 (d, J=6.0, 1H), 5.65–5.55 (m, 1H), 4.88 (s, 2H), 4.48 (d, J=3.9, 1H), 3.82 (s, 3H), 2.25–2.10 (m, 1H), 2.08–1.85 (m, 1H), 0.96–0.75 (m, 1H), 0.65–0.50 (m, 1H); MS m/z (M+Na) calcd 431, obsd 431.

Example 8-E

In a similar manner, resin (XIII-B) (153.2 mg) was treated with diethoxybutyraldehyde (1.5 mL) to afford compound II-8 (3.6 mg) which was isolated by preparative HPLC (Zorbax RX-8, 2.5×25 cm, 65% MeCN/water w/0.1% trifluoroacetic acid) and had the following properties: $^1$H NMR (DMSO-d$_6$) δ9.09(d, J=7.9, 1H), 8.81 (s, 1H), 7.81–7.73 (m, 3H), 7.48–7.35 (m, 3H), 7.24 (dd, J=7.6, 7.5, 1H), 6.85 (d, J=6.2, 1H), 5.63–5.59 (m, 1H), 4.86 (s, 2H), 4.61 (d, J=3.6, 1H), 3.82 (s, 3H), 2.21–2.13 (m, 1H), 1.96–1.90 (m, 1H), 0.87–0.79 (m, 1H), 0.61–0.56 (m, 1H); MS m/z (M+H) calcd 379, obsd 379.

Example 9

Preparation of Compound II-7a and Compound II-7b (Method A, FIG. 6)

Example 9-A

Preparation of (1,1-diethoxyethoxy)acetone

To a cold (0° C.) suspension of NaH (2.68 g, 60%) in THF (150 mL) was added a solution of 1,1-diethoxyethanol [which was prepared according to the literature procedure of Zirkle, C. L. et. al. *J. Org. Chem.* 1961, 26, 395–407] (9.00 g) in THF (20 mL), and the reaction mixture was stirred at room temperature for 1 hour before adding methallyl chloride (8.0 mL). The reaction mixture was heated to reflux overnight, cooled and filtered through a plug of celite. Solvent was removed by rotary evaporation, and the residue purified by column chromatography (silica, 20% ether/hexane) to give 1,1-diethoxyethyl methallyl ether (11.5, 90%). ozonolysis of a chilled (−30° C.) solution of this ether (6.00 g) in EtOAc (80 mL) was carried out until no starting material was detectable by TLC (1 hour). At this time, the reaction was purged with oxygen, treated with Pd(OH)$_2$ (150 mg) and stirred under an atmosphere of hydrogen overnight. The catalyst was filtered away, and the filtrate was concentrated by rotary evaporation. The resulting residue was purified by column chromatography (silica, 20% EtOAc/hexane) to afford the title compound (4.53 g, 82%).

Example 9-B

According to Method A (FIG. 6), resin (XIII-A) (230.2 mg) was treated with EtMgBr (1.25 mL) followed by (1,1-diethoxyethoxy)acetone (Example 8-A) (1.2 mL). After workup and cleavage from the resin, a portion of the crude reaction product mixture (10.5 mg) was taken up in methylene chloride (20 mL) and treated with BF$_3$ etherate (20 uL). After stirring for 2.5 hours, the solution was washed with saturated aqueous NaHCO$_3$ and brine prior to drying over MgSO$_4$. After filtration and solvent removal, the resulting residue was purified by preparative HPLC (Zorbax RX-8, 4×25 cm, 65% MeCN/water w/0.1% trifluoroacetic acid) to afford compound II-7a (2.34 mg) and compound II-7b (1.34 mg). Compound (II-7a) had the following properties: $^1$H NMR (CDCl$_3$) δ9.35–9.20 (m, 1H), 7.87 (d, J=7.6, 1H), 7.62 (d, J=7.0, 1H), 7.60–7.45 (m, 1H), 7.49 (dd, J=7.7, 7.5, 1H), 7.40 (d, J=8.1, 1H), 7.37–7.26 (m, 3H), 6.22 (s, 1H), 5.20–4.85 (m, 1H), 4.47 (s, 1H), 3.67 (d, J=12.7, 1H) 3.52 (d, J=11.8, 1H), 3.40 (d, J=12.7, 1H), 3.38 (d, J=11.8, 1H), 1.91 (s, 3H); MS m/z (M+H) calcd 409, obsd 409. Compound II-7b had the following properties: $^1$H NMR (CDCl$_3$) δ9.58–9.22 (m, 1H), 7.82 (d, J=7.4, 1H), 7.60–7.40 (m, 3H), 7.37–7.27 (m, 3H), 7.21 (d, J=8.1, 1H), 5.81 (s, 1H), 5.21 (s, 1H), 5.10–4.80 (m, 1H), 4.59 (d, J=13.5, 1H), 4.38 (dd, J=13.5, 5.3, 1H), 4.21 (d, J=13.1, 1H), 3.82 (d, J=13.2, 1H), 1.13 (s, 3H); MS m/z (M+H) calcd 409, obsd 409.

Example 10
Preparation of Compound II-5(FIG. 8)

To a solution of compound II-1(8.1 mg) in THF (2 mL) was added NBS (4.6 mg), and the reaction was stirred overnight. Additional NBS (4.5 mg) was added, and the reaction stirred for 2.5 hours. Insoluble material was filtered away and the filtrate was concentrated by rotary evaporation. The resulting residue was purified by column chromatography (C-18, 65% MeCN/water w/0.1% trifluoroacetic acid). The appropriate fractions were neutralized with NaHCO$_3$ and extracted into methylene chloride (3×20 mL) and dried over MgSO$_4$. After filtration and solvent evaporation, compound II-5 (5.1 mg) was obtained as white powder which had the following characteristics: $^1$H NMR (DMSO-d$_6$) δ9.22 (d, J=7.4, 1H), 8.67 (s, 1H), 8.14 (s, 1H), 7.86 (d, J=8.7, 1H), 7.72 (d, J=7.0, 1H), 7.63 (d, J=7.8, 1H), 7.42 (dd, J=7.5, 7.3, 1H), 7.35 (dd, J=7.3, 7.2, 1H), 6.86 (d, J=6.0, 1H), 5.63–5.58 (m, 1H), 4.94 (s, 2H), 4.54 (d, J=3.1, 1H), 2.30–2.14 (m, 1H), 2.00–1.82 (m, 1H), 0.96–0.88 (m, 1H), 0.62–0.50 (m, 1H); MS m/z (M+H) calcd 457/9 (1:1), obsd 457/9 (1:1).

Example 11
Preparation of Intermediate XV (FIG. 4)

To a solution of VIII-A [A$^1$,A$^2$=H$_2$, B$^1$,B$^2$=O, R$^3$=R$^4$=R$^5$=R$^6$=H)] (1.05 g) in DMF (25 mL) was added triethylamine (0.75 mL) and t-butyldimethylsilyl chloride (TBS-Cl) (0.65 g). After stirring for 3 hours, the reaction was quenched with saturated aqueous NaHCO$_3$ and extracted into EtOAc. The organic layer was washed with water and brine and dried over MgSO$_4$. After filtration and solvent evaporation, the resulting residue was triturated with ether to give compound XV (848 mg). The washings were evaporated to leave a residue that was purified by column chromatography (silica, 1% EtOAc/CH$_2$Cl$_2$) and gave additional product (502 mg, combined yield of 94%) that had the following spectral properties: $^1$H NMR (DMSO-d$_6$) δ11.94 (s, 1H), 9.32 (d, J=7.6, 1H), 8.03 (d, J=7.7, 1H), 7.64 (d, J=7.2, 1H), 7.58 (d, J=8.1, 1H), 7.44 (dd, J=7.7, 7.6, 1H), 7.39 (dd, J=7.7, 7.6, 1H), 7.32 (d, J=7.3, 1H), 7.25 (dd, J=7.6, 7.3, 1H), 5.00 (s, 2H), 4.14 (s, 2H), 0.99 (s, 9H), 0.46 (s, 6H); MS m/z (M+H) calcd 425, obsd 425.

Example 12
Preparation of Compound II-1 via Method B (FIG. 7)

A solution of Triton B in pyridine (0.45 M) was prepared by dissolving a 40% solution of Triton B in methanol (10 mL) in pyridine (10 mL). Solvent was removed under reduced pressure (20 mm Hg) to a final volume of ~8 mL. The residue was diluted with pyridine to 50 mL, filtered and stored under nitrogen. A solution of XV (20.3 mg) in pyridine (2.0 mL) was flushed with argon and treated with 300 μL of Triton B (0.45 M in pyridine) and diethoxybutyraldehyde (50 μL). After stirring for 2 hours, the reaction was extracted into EtOAc, washed with 1N aqueous HCl, brine and dried over MgSO$_4$. After filtration and solvent evaporation, the adduct was taken up in CH$_2$Cl$_2$ (10 mL) and treated with BF$_3$ etherate (10 μL). After stirring for 2.0 h, the solution was washed with saturated aqueous NaHCO$_3$ and brine prior to drying over MgSO$_4$. Removal of solvent by rotary evaporation gave a residue that was purified by preparative HPLC (Zorbax RX-8, 2.5×25 cm, 65% MeCN/water w/0.1% trifluoroacetic acid). The appropriate fractions were neutralized with NaHCO$_3$ and extracted into methylene chloride (3×20 mL) and dried over MgSO$_4$. After filtration and solvent evaporation, II-1(11.8 mg, 65% yield) was obtained whose $^1$H NMR and MS spectra and HPLC retention time were identical to material prepared and isolated by method A, described in Example 8-A.

Example 13
Preparation of Compound II-9(FIG. 8)

To a suspension of bromo compound II-5(6.2 mg) in 1-propanol (4.0 mL) was added 3-aminophenylboric acid (3.8 mg). After stirring for 0.25 hour, Pd(OAc)$_2$ (2.0 mg) Ph$_3$P (4.8 mg), Na$_2$CO$_3$ (2.8 mg), and water (2.0 mL) were sequentially added. The mixture was heated at reflux for 0.75 hour, cooled, extracted into CH$_2$Cl$_2$, and washed with water and brine. The organic layer was dried over MgSO$_4$, and solvent was removed by rotary evaporation to give a residue that was purified by preparative HPLC (Zorbax RX-8, 2.5×25 cm, 50% MeCN/water w/0.1% trifluoroacetic acid). The appropriate fractions were neutralized with NaHCO$_3$ and extracted into methylene chloride (3×20 mL) and dried over MgSO$_4$. After filtration and solvent evaporation, compound II-9(3.1 mg, 49% yield) was obtained and had the following spectral properties: $^1$H NMR (DMSO-d$_6$) δ9.22 (d, J=7.5, 1H), 8.66 (s, 1H), 8.00–7.25 (m, 8H), 7.12 (dd, J=7.1, 7.0, 1H), 6.95–6.80 (m, 3H), 6.53 (d, J=6.0, 1H), 5.63–5.58 (m, 1H), 4.99 (s, 2H), 4.55 (s, 1H), 2.25–2.10 (m, 1H), 1.95–1.90 (m, 1H), 0.98–0.88 (m, 1H), 0.65–0.57 (m, 1H); MS m/z (M+H) calcd 470, obsd 470.

Example 14
Preparation of Compound II-10(FIG. 9)

To a solution of compound II-1(5.0 mg) in DMSO (1 mL) was added NaCN (4.3 mg), and the mixture was warmed to 145° C. for 1 hour. The mixture was cooled, extracted into EtOAc, and washed with water (3×20 mL) and brine. The organic layer was dried over MgSO$_4$, filtered and evaporated to give a residue that was purified by preparative HPLC (Zorbax RX-8, 2.5×25 cm, 55% MeCN/water w/0.1% trifluoroacetic acid). The appropriate fractions were neutralized with NaHCO$_3$, extracted into methylene chloride (3×20 mL), and dried over MgSO$_4$. After filtration and solvent evaporation, compound II-10 (2.7 mg, 50% yield) was obtained and had the following spectral properties: $^1$H NMR (DMSO-d$_6$) δ11.4 (s, 1H), 8.86 (d, J=7.9, 1H), 8.79 (d, J=7.6, 1H), 7.90 (d, J=8.3, 1H), 7.62–7.55 5(m, 2H), 7.49 (dd, J=7.6, 7.4, 3H), 7.40 (dd, J=7.4, 7.3 1H), 7.35 (dd, J=7.5, 7.4, 1H), 6.86 (d, J=6.0, 1H), 6.03 (s, 1H), 5.40–5.30 (m, 1H), 2.25–2.14 (m, 1H), 2.03–1.90 (m, 1H), 1.10–0.98 (m, 1H), 0.82–0.77 (m, 1H).

Example 15
Preparation of Compound II-11.(Method A, FIG. 6)

According to the method A, resin (XIIIa) (150.2 mg) was reacted with EtMgBr (1.0 mL) followed by ethyl 2,5-dioxopentanoate [Schmidt, U., Reidl, B. *Synthesis*, 1993, 809] (1.5 mL). After workup and cleavage from the resin, the crude reaction product mixture was taken up in methylene chloride (20 mL) and treated with BF$_3$ etherate (20 μL). After stirring for 2.5 hours, the solution was washed with saturated aqueous NaHCO$_3$ and brine prior to drying over MgSO$_4$. After filtration and solvent removal, the resulting residue was purified by preparative HPLC (Zorbax RX-8, 4×25 cm, 55%–75% gradient MeCN/water w/0.1% trifluoroacetic acid) to afford compound II-11(6.4 mg) which had the following properties: $^1$H NMR (DMSO-d$_6$) δ9.36 (d, J=7.7, 1H), 8.68 (s, 1H), 8.00 (d, J=7.7, 1H), 7.83 (d, J=8.3, 1H), 7.58–7.15 (m, 5H), 6.97 (d, J=5.9, 1H), 4.93 (s, 2H), 4.82 (s, 1H), 4.48 (q, J=7.1, 2H), 2.42–1.91 (m, 2H), 1.37 (t, 3H, J=7.1), 1.25–0.63 (m, 2H).

Example 16
Preparation of Compound II-12

A solution of compound II-11(3.4 mg) in THF (2 mL) was treated with a 2 M solution of LiBH$_4$ (1.0 mL in THF) and the reaction was stirred for 1.5 hours. The reaction was quenched by the addition of 1 N aqueous HCl (4 mL). After stirring for 20 minutes, 10% aqueous NaOH (15 mL) was added and the mixture was extracted into methylene chloride (3×10 mL). After drying over $MgSO_4$, the mixture was filtered and solvent evaporated to afford compound II-12 (0.32 mg) which had the following properties: $^1H$ NMR (DMSO-$d_6$) δ9.35 (d, J=7.7, 1H), 8.62 (s, 1H), 7.98 (d, J=7.7, 1H), 7.83 (d, J=8.2, 1H), 7.75 (d, J=8.2, 1H), 7.50–7.25 (m, 4H), 6.84 (d, J=7.7, 1H), 6.11 (s, 1H), 4.91 (s, 2H), 4.71 (s, 3H), 4.50–4.40 (m, 1H), 4.30–4.20 (m, 1H) 2.42–1.91 (m, 2H), 1.25–0.63 (m, 2H); MS m/z (M+H) calcd. 409, obsd. 409.

Example 17
Preparation of Compound II-13

Following the procedure in Example 11, a solution of about 95-5 mixtures of VIII-C [A1,A2=H2,B1,B2=O, R3=R4=R5=H, R6=OMe)] and VIII-D [A1,A2=H2,B1,B2=O, R3=R4=R6=H, R5=OMe)] (1.25 g) was silylated in DMF (45 mL) with triethylamine (0.85 ml) and t-butyldimethyl silyl chloride (0.65 g) to afford VIIIB-TDBMS (1.41 g) which had the following spectral properties: $^1H$ NMR (DMSO-$d_6$) δ11.91 (s, 1H), 9.18 (d, J=8.6, 1H), 7.99 (d, J=7.8, 1H), 7.56 (d, J=8.0, 1H), 7.42 (dd, J=7.7, 7.6, 1H), 7.30–7.20 (m, 2H), 6.95 (dd, J=7.6, 2.5, 1H), 4.97(s, 2H), 4.09 (s, 2H), 3.81 (s, 3H), 0.99 (m, 9H), 0.45 (s, 6H). Also isolated by column chromatography was VIIID-TDBMS (65 mg) which had the following spectral properties: $^1H$ NMR (DMSO-$d_6$) δ11.92 (s, 1H), 9.01 (d, J=1.8, 1H), 8.02 (d, J=7.9, 1H), 7.58 (d, J=8.1, 1H), 7.53 (d, J=8.3, 1H), 7.44 (dd, J=7.2, 7.1, 1H), 7.25 (dd, J=7.2, 7.1, 1H), 6.91 (dd, J=8.1, 2.7, 1H), 4.99 (s, 2H), 4.06 (s, 2H), 3.78 (s, 3H), 0.99 (s, 9H), 0.46 (s, 6H).

Solution Phase Synthesis of Compound II-13

Following the procedure in Example 12, a solution of VIIID-TBDMS (10.3 mg) in pyridine (2.0 mL) was flushed with argon and treated with 350 μL of Triton B (0.45 M in pyridine) and diethoxybutyraldehyde (50 μL) (which was prepared according to the literature procedure of Paquette, L. A., Backhaus, D., Braum, R., Underiner, T. L., and Fuchs, K. J. Am. Chem. Soc. 1997, 119, 9662–71, the disclosure of which is hereby incorporated by reference in its entirety). After stirring for 2 hours, the reaction was extracted into EtOAc, washed with 10% aqueous $CuSO_4$ (3×50 mL), brine and dried over $MgSO_4$. After filtration and solvent evaporation, the residue was eluted through silica gel (30% EtOAc/hexane), and the UV active fraction was concentrated, taken up in $CH_2Cl_2$(4 mL) and treated with $BF_3$ etherate (10 μL). After stirring for 2.0 hours, the solution was washed with saturated aqueous $NaHCO_3$ and brine prior to drying over $MgSO_4$. Removal of solvent by rotary evaporation gave a residue that was triturated with ether to afford pure compound II-13 (4.6 mg,) which had the following spectral properties: $^1H$ NMR (DMSO-$d_6$) δ8.92 (d, J=2.3, 1H), 8.59 (s, 1H), 7.97 (d, J=7.7, 1H), 7.86 (d, J=8.3, 1H), 7.59 (d, J=8.2, 1H), 7.47 (dd, J=7.7, 7.6, 1H), 7.28 (dd, J=7.5, 7.4, 1H), 6.89 (dd, J=8.3, 2.4, 1H), 6.82 (d, J=6.0), 5.55–5.50 (m, 1H), 4.99 (s, 2H), 4.53 (d, J=3.5, 1H), 3.85 (s, 3H), 2.30–2.20 (m, 1H), 2.10–1.90 (m, 1H), 1.10–0.90 (m, 1H), 0.73–0.66 (m, 1H); MS m/z (M+H) calcd 409, obsd 409.

Example 18
Synthesis of Compound II-14a and Compound II-14b

Synthesis of VIIIA-TBDPS. To a solution of VIII-A (6.2 g) in DMF (150 mL) was added TEA (9.7 mL), t-butylchloro-diphenylsilane (tBDPS-Cl, 10.5 mL) and a catalytic amount of dimethylaminopyridine. The mixture was heated at 50 C. for 15 hours. Additional triethylamine (5.0 mL) and tBDPS-Cl (5.0 mL) was added and reaction was kept at 50 C. for another 20 hours. The reaction was quenched with $NaHCO_3$ and extracted into EtOAc. The organic layer was washed with water (2×100 mL) and brine before drying over MgSO4. After filtration and solvent evaporation, the resulting residue was triturated with 1:1 ether:hexane to afford product (9.1 g, 83%) of VIIIA-TBDPS, which had the following spectral properties: $^1H$ NMR (DMSO-$d_6$) δ11.95 (s, 1H), 9.21 (d, J=1.8, 1H), 7.80–7.20 (m, 16H), 7.13 (dd, J=8.1, 2.7, 1H), 4.83 (s, 2H), 4.13 (s, 2H), 1.25 (s, 9H) ); MS m/z (M+H) calcd 549, obsd 549.

Solution Phase Synthesis of II-17

A solution of VIIIA-TBDPS (102.5 mg) in pyridine (4.0 mL) was flushed with argon and treated with 1.0 mL of Triton B (0.45 M in pyridine) and diethoxybutyraldehyde (140 μL)) [which was prepared according to the literature procedure of Paquette, L. A., Backhaus, D., Braum, R., Underiner, T. L., and Fuchs, K. J. Am. Chem. Soc. 1997, 119, 9662–71]. After stirring for 2 hours, the reaction was extracted into EtOAc, washed with 10% aqueous $CuSO_4$ (3×50 mL) ), brine and dried over $MgSO_4$. After filtration and solvent evaporation, the residue was eluted through silica gel (30% EtOAc/hexane), and the UV active fraction was concentrated, taken up in $CH_2Cl_2$ (10 mL) and treated with $BF_3$ etherate (10 μL). After stirring for 0.5 hours, the solution was washed with saturated aqueous $NaHCO_3$ and brine prior to drying over $MgSO_4$. Removal of solvent by rotary evaporation gave a residue that was purified by column chromatography (silica gel, 25% EtOAc/hexane) to afford product (75.5 mg) and had the following spectral properties: $^1H$ NMR (DMSO-$d_6$) δ9.08 (d, J=7.2, 1H), 7.86 (d, J=8.2, 1H), 7.73 (d, J=6.9, 1H), 7.70–7.24 (m, 15H), 6.88 (d, J=5.9, 1H), 5.72 (m, 1H), 4.86 (s, 2H), 4.55 (d, J=3.3, 1H), 2.30–2.20 (m, 1H), 2.10–1.90 (m, 1H), 1.10–0.90 (m, 1H), 0.73–0.66 (m, 1H); MS m/z (M+Na) calcd 639, obsd 639.

Separation of the Enantiomers of TBDPS protected II-1a by chiral HPLC and preparation of Compounds II-14a and II-14b.

The TBDPS-protected II-1a was dissolved in minimum amounts of (1:4, v/v) $CHCl_3$: EtOH and 500 μL portions were injected on to a CHIRACEL OD column (1 cm ID×25 cm) and 100% ethanol (1.5 mL/min) was used as an eluent. Fractions from each run corresponding to enatiomer A (24.0–27.0 min) and enantiomer B (36.0–39.0 min) were collected and were concentrated saparatly. The individual enantiomers of TBDPS protected II-1a were taken up in THF (12 mL) and added to a 0.1 M aqueous solution of KF (4.6 mL) buffered with HF (0.125 mL of a 0.1 M aqueous solution). Each solution was stirred for 40 hours. The solution was taken up in DCM and washed with aqueous $NaHCO_3$. The aqueous layer was extracted with DCM (3×100 mL) and the combined organic layers were immediately passed through a plug of $MgSO_4$ and evaporated to leave a residue that was triturated with 1:1 ether:hexane and purified by preparative HPLC as described in example 8-A. The HPLC retention times and MS spectral data of each enantiomer corresponded to authentic II-1a. Compound II-14a (2.84 mg) was obtained in 97% ee and compound II-14b (3.52 mg) was obtained in 90% ee as determined by chiral HPLC. Chiral Purity of the indivisual enetimers was determined using CHIRACEL OD column (0.46 cm ID×5 cm) using 1:1 methanol/ethanol as eluent (0.25 mL/min). $R_t$=for II-14a: 14.0 min and $R_t$=for II-14b: 20.5 min.

Example 19
Synthesis of Compound II-15

To a suspension of VIII-A (1 g, 3.2 mmol) in THF (40 mL) was added NBS (632 mg, 3.5 mmol), and the reaction was stirred at room temperature for 18 hours. The solvent was removed under vacuum and the resultant yellow-orange solid was suspended in methanol (50 mL). The slurry was filtered and the solid washed with more methanol. After drying, the bromo compound ($R^3$=Br) (1.09 g, 2.8 mmol, 88% yield) was recovered as a pale yellow solid: (MS: m/z (M+H) 389, 391).

To a solution of the above bromide (1.09 g, 2.8 mmol) in benzene (60 mL) and N-methylpyrrolidinone (6 mL) was added 4,4'-dimethoxybenzhydrol (818 mg, 3.4 mmol) and p-toluenesulfonic acid (532 mg, 2.8 mmol), and the mixture was heated to reflux. After 24 hours the reaction was cooled to room temperature and diluted with ethyl acetate (200 mL). The organic layer was washed with NaHCO3 (2×), $H_2O$ (2×), and brine(2×). The organic layer was dried over anhydrous $MgSO_4$, filtered and solvent was removed in vacuo. The crude material was purified via column chromatography (10% EtOAc-hexane) to provide the desired DMB protected 3-bromo indole derivative (1.5 g, 2.4 mmol, 87% yield) as an orange solid: (MS m/z (M+H) 615, 617).

A 250 mL sealable tube was charged with the DMB protected 3-bromo compound (1.5 g, 2.4 mmol), bis(triphenylphosphinyl)palladium dichloride (100 mg, 0.14 mmol), anhydrous sodium acetate (3.9 g, 4.8 mmol), and methoxyethanol (50 mL). The tube was alternately evacuated and filled with CO, leaving it under an atmosphere of CO. It was then lowered into an oil bath at 150° C. After 4 hours the tube was cooled to room temperature and recharged with CO. This was repeated once more with the reaction going a total of 10 hours. The reaction was diluted with ethyl acetate (250 mL), washed with water, dried over anhydrous $MgSO_4$, filtered and dried in vacuo. The redidue was triturated with methanol to give the 3-carboxy compound (1.29 g, 2.02 mmol, 84% yield) as a yellow solid: MS m/z (M+H) 639.

To a solution of the above ester (1.2 g, 1.9 mmol) in methylene chloride (20 mL) was added thioanisole (1 mL) followed by TFA (4 mL). After stirring for 1 hours at room temperature, the reaction mixture was evaporated to dryness and the residue was suspended in diethylether. The suspension was filtered, and the solid was washed with diethylether until the filtrate was colorless. The solid was dried in vacuo to afford the ester (636 mg, 1.54 mmol) as an off-white solid: MS m/z (M+H) 413.

The above ester (500 mg, 1.2 mmol) was suspended in methylene chloride (15 mL) and a solution of diisobutyl aluminumhydride in methylene chloride (5.5 mL, 5.5 mmol, 1.0 M) was added. After 2 hours at room temperature the reaction was quenched with methanol. Solvent was removed by rotary evaporation, and water was added to the reisude. The slurry was filtered and the solid dried in vacuo. The desired product [$A_1,A_2$=O, $B_1,B_2$=$H_2$, R3=3—$CH_2OH$, R4=R5=R6=H, Q=NH] (367 mg, 1.08 mmol) was obtained as a pale yellow solid: MS m/z (M+H) 341 m/e.

The above alcohol (360 mg, 0.9 mmol) [$A_1,A_2$=O, $B_1B_2$=$H_2$, R3=3-$CH_2OH$, R4=R5=R6=H, Q=NH] was placed in a sealable tube with ethanol (15 mL). To this suspension was added trifluoroacetic anhydride (254 mL, 1.8 mmol). The reaction was heat at 70° C. for 15 hours. The tube was cooled and solvent was removed in vacuo. The resulting solid was triturated with methanol, filtered, and dried to afford the desired ether (239 mg, 0.65 mmol, 72% yield) as an orange solid: MS m/z (M+H) 369.

Following the procedure in example 11, the above ether (100 mg, 0.27 mmol) was silylated in DMF (5 mL) with triethylamine (0.75 mL, 0.54 mmol) ) and t-butyldimethylsilyl chloride (81.0 mg, 0.54 mmol). After aqueous workup and solvent evaporation, the solid was triturated with ether:hexane (1:1) to afford product (114.6 mg, 0.24 mmol, 88%) as an orange solid: MS m/z (M+H) 483.

Following the procedure in example 12, a solution of the above ether (23.0 mg, 0.048 mmol) in pyridine (4.0 mL) was flushed with argon and treated with 200 µL of Triton B (0.45 M in pyridine) and 5,5-dimethyl-1,3-dioxane-2-propionaldehyde (50 µL). Khanna, I. K.; Weier, R. M.; Yu. Y.; Collins, P. W.; Miyashiro, J. M.; et. al., *J. Med. Chem.* 1997, 40, 1619–33 hereby incorporated by reference in its entirety. After 0.5 hours, additional Triton B (200 µL of 0.45 M in pyridine) was added. This was repeated twice more. Finally, the reaction was extracted into EtOAc, washed with 10% aqueous $CuSO_4$ (3×50 mL), brine and dried over $MgSO_4$. After filtration and solvent evaporation, the residue was eluted through silica gel (30% EtOAc/hexane), and the UV active fraction was concentrated, taken up in $CH_2Cl_2$ (4 mL) and treated with a catalytic amount of pyridinium tosylate (1 mg). The mixture was heated to reflux for 48 hours, and then solvent was removed in vacuo. The resulting residue was taken up in THF (8.0 mL) and added to to a 0.1 M aqueous solution of KF (2.9 mL) buffered with HF (0.09 mL of a 0.1 M aqueous solution). After stirring for 20 hours, the solution was extracted into DCM and washed with aqueous $NaHCO_3$. The aqueous layer was extracted with DCM (3×100 mL) and the combined organic layers were immediately passed through a plug of $MgSO_4$ and evaporated to leave a residue that was triturated with 1:1 ether:hexane and purified by preparative HPLC as described in example 8-A. This afforded the desired product II-15 (1.26 mg, 6.0%) which had the following spectral properties: $^1$H NMR (DMSO-$d_6$) δ9.41 (d, J=2.3, 1H), 8.53 (s, 1H), 7.90 (s, 1H), 7.80–7.25 (m, 5H), 6.33 (d, J=6.0, 1H), 5.31 (m, 1H), 4.95 (s, 2H), 4.66 (s, 2H), 4.48 (m, 1H), 3.50(q, J=6.8, 2H), 2.30–2.20 (m, 1H), 2.10–1.90 (m, 1H), 1.25 (t, J=6.8, 3H, 1.10–0.90 (m, 1H), 0.73–0.66 (m, 1H); MS m/z (M+H) calcd 437, obsd 437.

Example 20

Synthesis of Compound II-1b

Preparation of XIV (DMB-VIIIA). A three neck round bottom flask fitted with an overhead mechanical stirrer and a Dean-Stark trap was sequentially charged with DMB-OH (2.44 g, 10 mmoles), 1-methyl-2-pyrolidinone (30 mL), benzene (270 mL), VIII-A (3.10 g, 10 mmol) and p-toluenesulfonic acid (1.90 g, 10 mmoles). The reaction mixture was heated to reflux. After 2 hours, the reaction mixture became homogenous, and heating was continued for another 2 hours. The reaction mixture was cooled to room temperature, diluted with EtOAc (200 mL), washed with saturated aqueous NaHCO3 solution (4×100 mL), water (4×100 mL), and the organic layer was dried over anhydrous MgSO4, filtered and concentrated in-vacuo. The residue was triturated with EtOAc/hexane and the resulting solid was filtered and dried under high vacuum to afford XIV (FIG. 4) [A1,A2=H2, B1,B2=O, R3=R4=R5=R6=H, Q=NH, R'=R"=H], (5.2 g, 98%) which had the following spectral properties: $^1$H NMR (CDCl$_3$-$d_6$) δ9.54 (d, J=7.82, 1H), 8.55 (s, 1H), 7.68 (d, J=7.8 1H), 7.60–6.70 (m, 15H), 4.71 (s, 2H), 4.03 (s, 2H), 3.78 (s, 6H); MS m/z (M+H) calcd 537, obsd 537.

To a solution of XIV (FIG. 4) (102.5 mg) in THF (6.0 mL) was added a THF solution of EtMgBr (0.8 mL of a 1.0 M) and the mixture was stirred for 1 hour. 5,5-dimethyl-1,3-dioxane-2-propionaldehyde (300 µL) [which was prepared according to the literature procedure Khanna, I. K.; Weier, R. M.; Yu. Y.; Collins, P. W.; Miyashiro, J. M.; et. al.,*J. Med. Chem.* 1997, 40, 1619–33] was added, and the mixture was stirred for 3 hours. The reaction was quenched with aqueous $NH_4$ Cl and extracted into EtOAc. The organic layer was washed with saturated aqueous $NaHCO_3$ and brine prior to drying over $MgSO_4$. Removal of solvent by rotary evaporation gave a residue that was purified by column chromatography (silica gel, 40% EtOAc/hexane) to yield two fractions corresponding to the two diastereomeric adducts: MS m/z (M+H) 709. The more polar fraction (25 mg) was taken up in dichloromethane (10 mL) and treated with BF3 etherate (10 μL).

After stirring for 1.5 hours, the solution was washed with saturated aqueous NaHCO3 solution, and brine, and the organic layer was dried over anhydrous MgSO$_4$, filtered and concentrated in-vacuo. The resulting residue was purified by preparative HPLC as described in example 8-A to afford the product (1.75 mg) which had the following spectral properties: $^1$H NMR (DMSO-d$_6$) δ9.20 (d, J=7.46, 1H), 8.56 (s, 1H), 7.97 (d, J=7.7, 1H), 7.69 (d, J=8.2, 1H), 7.57 (d, J=7.3, 1H), 7.52–7.20 (m, 4H), 6.57 (m, 1H), 5.1 (m, 1H), 4.88 (s, 2H), 4.67 (s, 1H), 2.30–2.20 (m, 1H), 2.10–1.90 (m, 1H), 1.10–0.90 (m, 1H), 0.73–0.66 (m, 1H); MS m/z (M+H) calcd 379, obsd 379.

Example 21

Synthesis of Compounds II-16a and II-16b

To a solution of VIIIA-TBDPS (see example 18) (214 mg) in pyridine (4.0 mL) was flushed with argon and treated with 750 μL of Triton B (0.45 M in pyridine) and a solution of 2,2-diethoxy-ethoxy-acetaldehyde (200 mg) [which was prepared according to the literature procedure of: Aparico, F. J. L.; Benitez, F. Z.; Gonzalez, F. S.; *Carbohydr. Res.* 1983, 297–302 the disclosure of which is hereby incorporated by reference in its entirety], in pyridine (2 mL). Additional Triton B (250 μL) added after 2 hours. After stirring another 0.5 hours, the reaction was extracted into EtOAc, washed with 10% aqueous CuSO$_4$ (3×50 mL), brine and dried over MgSO$_4$. After filtration and solvent evaporation, the residue was eluted through silica gel (35% EtOAc/hexane), and the UV active fraction was concentrated, taken up in CH$_2$Cl$_2$ (10 mL) and treated with BF$_3$ etherate (10 uL). After stirring for 0.5 hours, the solution was washed with saturated aqueous NaHCO$_3$ and brine prior to drying over MgSO$_4$. Removal of solvent by rotary evaporation gave a residue that was purified by column chromatography (silica gel, 35% EtOAc/hexane) to yield two fractions corresponding to the two diastereomeric adducts: MS m/z (M+H) 725. Each adduct was taken up in CH$_2$Cl$_2$ (10 mL) and treated with BF$_3$ etherate (10 μL). After stirring for 0.5 hours, solvent was removed by rotary evaporation and each residue was taken up in THF (15 mL) and added to a 0.1 M aqueous solution of KF (5.8 mL) buffered with HF (0.20 mL of a 0.1 M aqueous solution). Each solution was stirred for 20 hours, extracted into DCM and washed with aqueous NaHCO3. The aqueous layer was extracted with DCM (3×100 mL) and the combined organic layers were immediately passed through a plug of MgSO4 and evaporated. The resulting pair of residues were taken up in CH$_2$Cl$_2$ (10 mL) and treated with BF$_3$ etherate (10 μL) and stirred for 48 hours.

Each reaction mixture was extracted into CH$_2$Cl$_2$ and washed with saturated aqueous NaHCO$_3$ and brine prior to drying over MgSO$_4$. Removal of solvent by rotary evaporation gave a residue that was purified by preparative HPLC as described in example 8-A. One diasteromer, compound II-16a, (2.38 mg isolated) had the following spectral properties: $^{13}$C NMR (DMSO-d$_6$) δ172.0, 142.6, 142.5, 142.1, 141.0, 139.8, 134.8, 130.6, 128.0, 127.2, 127.0, 126.6, 124.4, 124.2, 122.7, 121.7, 121.0, 116.8, 112.1, 80.0, 70.0, 69.1, 65.6, 54.1, 45.7; $^1$H NMR (DMSO-d$_6$) δ9.23 (d, J=7.7, 1H), 8.58 (s, 1H), 7.99 (d, J=7.7, 1H), 7.77 (d, J=8.3, 1H), 7.63 (d, J=7.22, 1H), 7.48–7.30 (m, 4H), 6.56 (s, 1H), 5.10 (m, 1H), 4.90 (s, 2H), 4.70 (m, 1H), 3.80–3.60 (m, 2H), 3.30–3.00 (m, 2H) MS m/z (M+Na) calcd 395, obsd 395.

The other diastereomer, compound II-16b, (1.00 mg isolated) had the following spectral properties: $^1$H NMR (DMSO-d$_6$) δ9.21 (d, J=7.7, 1H), 8.59 (s, 1H), 7.99 (d, J=7.7, 1H), 7.77–7.30 (m, 6H), 5.95 (s, 1H), 5.05 (m, 1H), 4.91 (s, 2H), 4.63 (m, 1H), 4.55–4.30 (m, 2H), other signals lost under solvent peak; MS m/z (M+Na) calcd 395, obsd 395.

Compounds of Formula II may be further understood by reference to Table 9 which sets forth certain preferred embodiments designated as Formula III, wherein the chiral centers (*) are specified. Values for R$^1$, R$^4$, R$^6$, and R$^7$ are H; Y is O; and n is 1.

TABLE 9

III

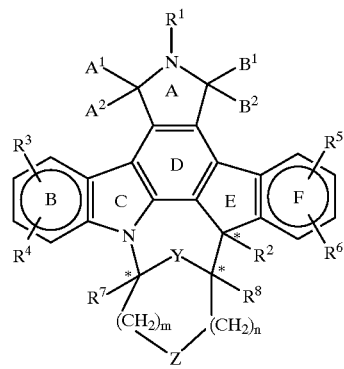

| Comp. No. | A$_1$A$_2$ | B$_1$B$_2$ | R$_2$ | R$_3$ | R$_5$ | R$_8$ | Z | m | R2 R7 R8 |
|---|---|---|---|---|---|---|---|---|---|
| III-A1 | H,H | O | H | H | H | H | bond | 1 | R S R |
| III-A2 | H,H | O | H | H | H | H | bond | 1 | S S R |
| III-A3 | H,H | O | H | H | H | H | bond | 1 | R R S |
| III-A4 | H,H | O | H | H | H | H | bond | 1 | S R S |
| III-B1 | H,H | O | Et | H | H | H | bond | 1 | R S R |
| III-B2 | H,H | O | Et | H | H | H | bond | 1 | S S R |
| III-B3 | H,H | O | Et | H | H | H | bond | 1 | R R S |
| III-B4 | H,H | O | Et | H | H | H | bond | 1 | S R S |
| III-C1 | H,H | O | H | H | H | Me | bond | 1 | R S R |
| III-C2 | H,H | O | H | H | H | Me | bond | 1 | S S R |

TABLE 9-continued

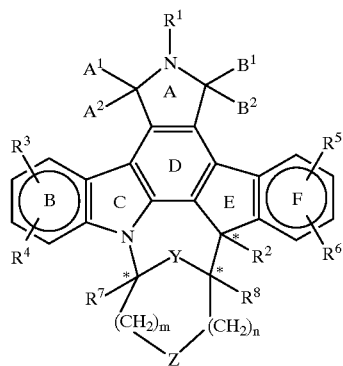

III

| Comp. No. | $A_1A_2$ | $B_1B_2$ | $R_2$ | $R_3$ | $R_5$ | $R_8$ | Z | m | R2 R7 R8 |
|---|---|---|---|---|---|---|---|---|---|
| III-C3 | H,H | O | H | H | H | Me | bond | 1 | R R S |
| III-C4 | H,H | O | H | H | H | Me | bond | 1 | S R S |
| III-D1 | H,H | O | H | H | H | Me | bond | 2 | R R R |
| III-D2 | H,H | O | H | H | H | Me | bond | 2 | S R S |
| III-D3 | H,H | O | H | H | H | Me | bond | 2 | R S R |
| III-D4 | H,H | O | H | H | H | Me | bond | 2 | S S R |
| III-E1 | H,H | O | H | 3-Br | H | Me | bond | 1 | R S R |
| III-E2 | H,H | O | H | 3-Br | H | Me | bond | 1 | S S R |
| III-E3 | H,H | O | H | 3-Br | H | Me | bond | 1 | R R S |
| III-E4 | H,H | O | H | 3-Br | H | Me | bond | 1 | S R S |
| III-F1 | H,H | O | H | H | 10-OMe | H | bond | 1 | R S R |
| III-F2 | H,H | O | H | H | 10-OMe | H | bond | 1 | S S R |
| III-F3 | H,H | O | H | H | 10-OMe | H | bond | 1 | R R S |
| III-F4 | H,H | O | H | H | 10-OMe | H | bond | 1 | S R S |
| III-G1 | H,H | O | H | H | H | Me | O | 1 | S S S |
| III-G2 | H,H | O | H | H | H | Me | O | 1 | R S S |
| III-G3 | H,H | O | H | H | H | Me | O | 1 | R R R |
| III-G4 | H,H | O | H | H | H | Me | O | 1 | S R R |
| III-H1 | O | H,H | H | H | H | H | bond | 1 | R S R |
| III-H2 | O | H,H | H | H | H | H | bond | 1 | S S R |
| III-H3 | O | H,H | H | H | H | H | bond | 1 | R R S |
| III-H4 | O | H,H | H | H | H | H | bond | 1 | S R S |
| III-I1 | H,H | O | H | 3-(3'-$NH_2$—Ph) | H | H | bond | 1 | R S R |
| III-I2 | H,H | O | H | 3-(3'-$NH_2$—Ph) | H | H | bond | 1 | S S R |
| III-I3 | H,H | O | H | 3-(3'-$NH_2$—Ph) | H | H | bond | 1 | R R S |
| III-I4 | H,H | O | H | 3-(3'-$NH_2$—Ph) | H | H | bond | 1 | S R S |
| III-J1 | O | O | O H | H | H | H | bond | 1 | S S R |
| III-J2 | O | O | O H | H | H | H | bond | 1 | R S R |
| III-J3 | O | O | O H | H | H | H | bond | 1 | R R S |
| III-J4 | O | O | O H | H | H | H | bond | 1 | S R S |
| III-K1 | H,H | O | H | H | H | CO2—Et | bond | 1 | R S R |
| III-K2 | H,H | O | H | H | H | CO2—Et | bond | 1 | S S R |
| III-K3 | H,H | O | H | H | H | CO2—Et | bond | 1 | R R S |
| III-K4 | H,H | O | H | H | H | CO2—Et | bond | 1 | S R S |
| III-L1 | H,H | O | H | H | H | CH2OH | bond | 1 | R S R |
| III-L2 | H,H | O | H | H | H | CH2OH | bond | 1 | S S R |
| III-L3 | H,H | O | H | H | H | CH2OH | bond | 1 | R R S |
| III-L4 | H,H | O | H | H | H | CH2OH | bond | 1 | S R S |
| III-M1 | H,H | O | H | H | 9-OMe | H | Bond | 1 | R S R |
| III-M2 | H,H | O | H | H | 9-OMe | H | Bond | 1 | S S R |
| III-M3 | H,H | O | H | H | 9-OMe | H | Bond | 1 | R R S |
| III-M4 | H,H | O | H | H | 9-OMe | H | Bond | 1 | S R S |
| III-N1 | H,H | O | H | H | H | H | bond | 1 | R S R |
| III-N2 | H,H | O | H | H | H | H | bond | 1 | S S R |
| III-N3 | H,H | O | H | H | H | H | bond | 1 | R R S |
| III-N4 | H,H | O | H | H | H | H | bond | 1 | S R S |
| III-P1 | H,H | O | H | 3-CH2O—CH2OEt | H | H | bond | 1 | R S R |
| III-P2 | H,H | O | H | 3-CH2O—CH2OEt | H | H | bond | 1 | S S R |
| III-P3 | H,H | O | H | 3-CH2O—CH2OEt | H | H | bond | 1 | R R S |
| III-P4 | H,H | O | H | 3-CH2O—CH2OEt | H | H | bond | 1 | S R S |
| III-Q1 | H,H | O | H | H | H | H | O | 1 | R S S |
| III-Q2 | H,H | O | H | H | H | H | O | 1 | S S S |

TABLE 9-continued

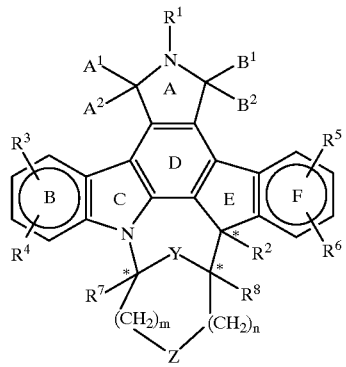

| Comp. No. | A₁A₂ | B₁B₂ | R₂ | R₃ | R₅ | R₈ | Z | m | R2 | R7 | R8 |
|---|---|---|---|---|---|---|---|---|---|---|---|
| III-Q3 | H,H | O | H | H | H | H | O | 1 | R | R | R |
| III-Q4 | H,H | O | H | H | H | H | O | 1 | S | R | R |

It is intended that each of the patents, applications, and printed publications mentioned in this patent document be hereby incorporated by reference in their entirety. As those skilled in the art will appreciate, numerous changes and modifications may be made to the preferred embodiments of the invention without departing from the spirit of the invention. It is intended that all such variations fall within the scope of the invention.

What is claimed is:

1. A compound of the formula:

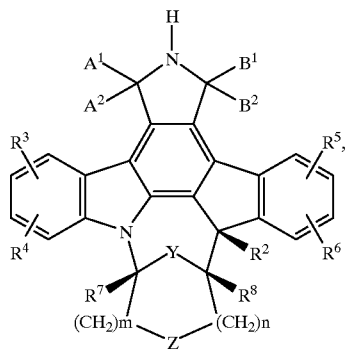

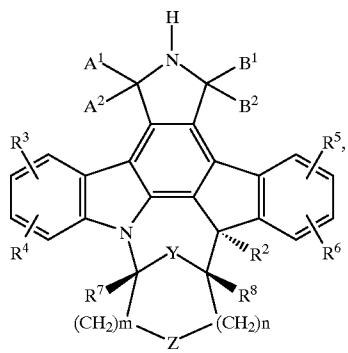

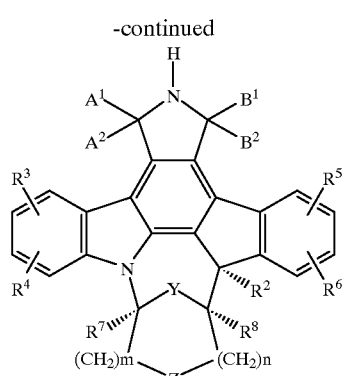

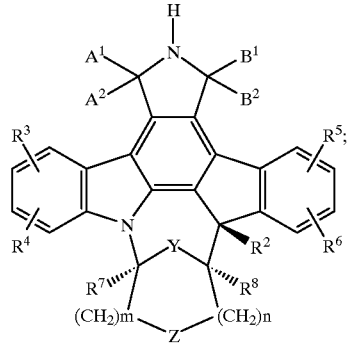

wherein:

$R^2$ is selected from the group consisting of H, alkyl having from 1 to 4 carbons, —OH, alkoxy having from 1 to 4 carbons, —OC(=O)$R^9$, —OC(=O)N$R^{11}R^{12}$, —O(CH$_2$)$_p$N$R^{11}R^{12}$, —O(CH$_2$)$_p$O$R^{10}$, substituted or unsubstituted arylalkyl having from 6 to 10 carbons, and substituted or unsubstituted heteroarylalkyl;

$R^3$, $R^4$, $R^5$ and $R^6$ are each independently selected from the group consisting of:

a) H, aryl, heteroaryl, F, Cl, Br, I, —CN, CF$_3$, —NO$_2$, —OH, —O$R^9$, —O(CH$_2$)$_p$N$R^{11}R^{12}$, —OC(=O)$R^9$, —OC(=O)N$R^2R^7$, —OC(=O)N$R^{11}R^{12}$, —O(CH$_2$)$_p$O$R^{10}$, —CH$_2$O$R^{10}$, —N$R^{11}R^{12}$, —N$R^{10}$S(=O)$_2R^9$, —N$R^{10}$C(=O)$R^9$, b) —CH$_2$OR$^{14}$, wherein R$^{14}$ is the residue of an amino acid after the hydroxyl group of the carboxyl group is removed;

c) —NR$^{10}$C(=O)NR$^{11}$R$^{12}$, —CO$_2$R$^2$, —C(=O)R$^2$, —C(=O)NR$^{11}$R$^{12}$, —CH=NOR$^2$, —CH=NR$^9$, —(CH$_2$)$_p$NR$^{11}$R$^{12}$, —(CH$_2$)$_p$NHR$^{14}$, or —CH=NNR$^2$R$^{2A}$ wherein R$^{2A}$ is the same as R$^2$;

d) —S(O)$_y$R$^2$—(CH$_2$)$_p$S (O)$_y$R$^9$, —CH$_2$S(O)$_y$R$^{14}$ wherein y is 0, 1 or 2;

e) alkyl having from 1 to 8 carbons, alkenyl having from 2 to 8 carbons, and alkynyl having 2 to 8 carbons, wherein:
  1) each alkyl, alkenyl, or alkynyl group is unsubstituted; or
  2) each alkyl, alkenyl, or alkynyl group is substituted with 1 to 3 groups selected from the group consisting of aryl having from 6 to 10 carbons, heteroaryl, arylalkoxy, heterocycloalkoxy, hydroxyalkoxy, alkyloxy-alkoxy, hydroxyalkylthio, alkoxy-alkylthio, F, Cl, Br, I, —CN, —NO$_2$, —OH, —OR$^9$, —X$^2$(CH$_2$)$_p$NR$^{11}$R$^{12}$, —X$^2$(CH$_2$)$_p$C(=O)NR$^{11}$R$^{12}$, —X$^2$(CH$_2$)$_p$OC(=O)NR$^{11}$R$^{12}$, —X$^2$(CH$_2$)$_p$CO$_2$R$^9$, —X$^2$(CH$_2$)$_p$S(O)$_y$R$^9$, —X$^2$(CH$_2$)$_p$NR$^{10}$C(=O)NR$^{11}$R$^{12}$, —OC(=O)R$^9$, —OCONHR$^2$, —O-tetrahydropyranyl, —NR$^{11}$R$^{12}$, —NR$^{10}$C(=O)R$^9$, —NR$^{10}$CO$_2$R$^9$, —NR$^{10}$C(=O)NR$^{11}$R$^{12}$, —NHC(=NH)NH$_2$, NR$^{10}$S(O)$_2$R$^9$, —S(O)$_y$R$^9$, —CO$_2$R$^2$, —C(=O)NR$^{11}$R$^{12}$, —C(=O)R$^2$, —CH$_2$OR$^{10}$, —CH=NNR$^2$R$^{2A}$, —CH=NOR$^2$, —CH=NR$^9$, —CH=NNHCH(N=NH)NH$_2$, —S(=O)$_2$NR$^2$R$^{2A}$, —P(=O)(OR$^{10}$)$_2$, —OR$^{14}$, and a monosaccharide having from 5 to 7 carbons wherein each hydroxyl group of the monosaccharide is independently either unsubstituted or is replaced by H, alkyl having from 1 to 4 carbons, alkylcarbonyloxy having from 2 to 5 carbons, or alkoxy having from 1 to 4 carbons;

X$^2$ is O, S, or NR$^{10}$;

R$^7$ and R$^8$ are each independently selected from the group consisting of H, alkyl having from 1 to 4 carbons, alkoxy having from 1 to 4 carbons, substituted or unsubstituted arylalkyl having from 6 to 10 carbons, substituted or unsubstituted heteroarylalkyl, —(CH$_2$)$_p$OR$^{10}$, —(CH$_2$)$_p$OC(=O)NR$^{11}$R$^{12}$, and —(CH$_2$)$_p$NR$^{11}$R$^{12}$; or R$^7$ and R$^8$ together form a linking group of the formula —CH$_2$—X$^3$—CH$_2$—, wherein X$^3$ is X$^2$ or a bond;

R$^9$ is selected from the group consisting of alkyl, aryl and heteroaryl;

R$^{10}$ is selected from the group consisting of H and alkyl having from 1 to 4 carbons;

R$^{11}$ and R$^{12}$ are each independently selected from the group consisting of H and alkyl having from 1 to 4 carbons; or R$^{11}$ and R$^{12}$ together form a linking group of the formula —(CH$_2$)$_2$—X$^1$—(CH$_2$)$_2$—, wherein X$^1$ is selected from the group consisting of —O—, —S—, and —CH$_2$—;

m and n are each independently 0, 1, or 2;

p is 1 to 4;

Y is selected from the group consisting of —O—, —S—, —N(R$^{10}$)—, —N$^+$(O$^-$)(R$^{10}$)—, —N(OR$^{10}$)—, and —CH$_2$—;

Z is selected from the group consisting of a bond, —O—, —CH=CH—, —S—, —C(=O)—, —CH(OR$^{10}$)—, —N(R$^{10}$)—, —N(OR$^{10}$)—, CH(NR$^{11}$R$^{12}$)—, —C(=O)N(R$^{17}$)—, —N(R$^{17}$)C(=O)—, —N(S(O)$_y$R$^9$)—, —N(S(O)$_y$NR$^{11}$R$^{12}$)—, —N(C(=O)R$^{17}$)—, —C(R$^{15}$R$^{16}$)—, —N$^+$(O$^-$)(R$^{10}$)—, —CH(OH)—CH(OH)—, and —CH(O(C=O)R$^9$)CH(OC(=O)R$^{9A}$)—, wherein R$^{9A}$ is the same as R$^9$;

R$^{15}$ and R$^{16}$ are independently selected from the group consisting of H, —OH, —C(=O)R$^{10}$, —O(C=O)R$^9$, hydroxyalkyl, and —CO$_2$R$^{10}$;

R$^{17}$ is selected from the group consisting of H, alkyl, aryl, and heteroaryl;

A$^1$ and A$^2$ are selected from the group consisting of H, H; H, OR$^2$; H, —SR$^2$; H, —N(R$^2$)$_2$; and a group wherein A$^1$ and A$^2$ together form a moiety selected from the group consisting of =O, =S, and =NR$^2$;

B$^1$ and B$^2$ are selected from the group consisting of H, H; H, —OR$^2$; H, —SR$^2$; H, —N(R$^2$)$_2$; and a group wherein B$^1$ and B$^2$ together form a moiety selected from the group consisting of =O, =S, and =NR$^2$;

with the proviso that at least one of the pairs A$^1$ and A$^2$, or B$^1$ and B$^2$, form =O.

2. The compound of claim 1 wherein A$^1$A$^2$ and B$^1$B$^2$ are independently =O or H,H.

3. The compound of claim 2 wherein Y is O.

4. The compound of claim 3 wherein Z is a bond, O, S, or substituted or unsubstituted N.

5. The compound of claim 4 wherein m and n are independently 1 or 2.

6. The compound of claim 5 wherein R$^2$ is H, hydroxyl, or substituted or unsubstituted alkyl.

7. The compound of claim 6 wherein R$^3$, R$^4$, R$^5$, and R$^6$ are independently H, substituted or unsubstituted alkyl, halogen, substituted or unsubstituted alkoxy, substituted or unsubstituted amino, substituted or unsubstituted aryl, or OR$^9$.

8. The compound of claim 7 wherein R$^7$ and R$^8$ are independently H, alkyl having from 1 to 4 carbons, alkoxy having from 1 to 4 carbons or —(CH$_2$)$_p$OR$^{10}$.

9. The compound of claim 1 wherein R$^4$, R$^6$, and R$^7$ are H, Y is O, n is 1, A$^1$A$^2$ and B$^1$B$^2$ are independently =O or H, H; R$^2$ is H, OH or lower alkyl, n is 1, m is 1 or 2, and Z is a bond or O.

10. The compound of claim 9 wherein R$^3$ and R$^5$ are each independently H, substituted or unsubstituted alkyl, halogen, substituted or unsubstituted alkoxy, substituted or unsubstituted amino, substituted or unsubstituted aryl, or —OR$^9$.

11. The compound of claim 9 wherein R$^8$ is H, alkyl having from 1 to 4 carbons, alkoxy having from 1 to 4 carbons or —(CH$_2$)$_p$OR$^{10}$.

12. The compound of claim 11 having the formula:
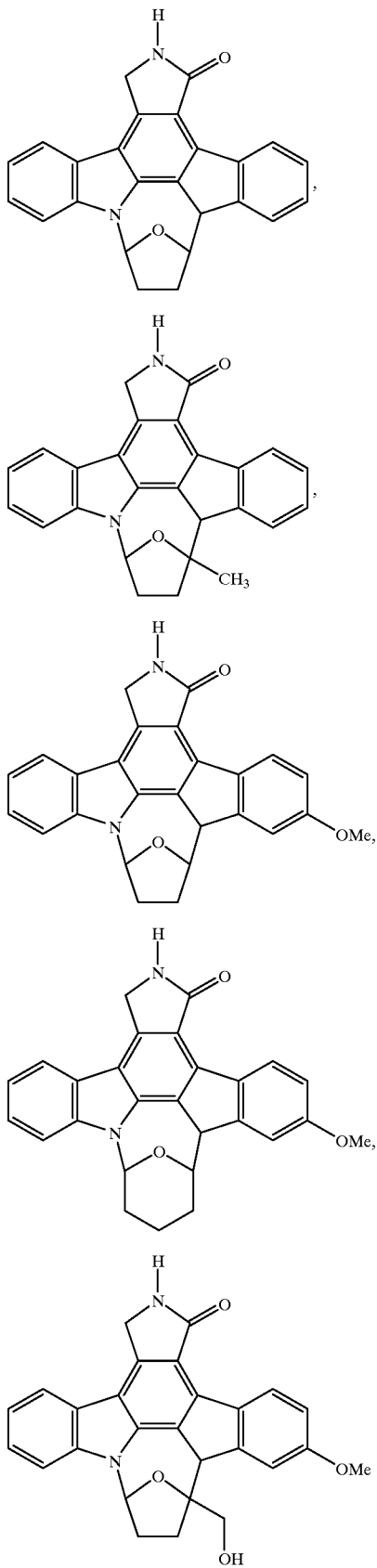
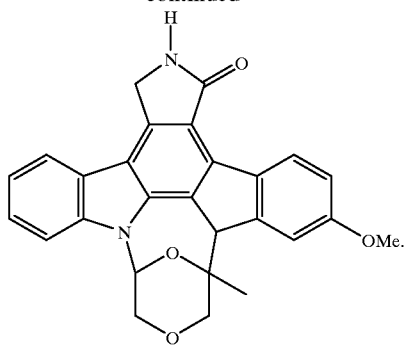
13. The compound of claim 12 having enantiomers of formula:
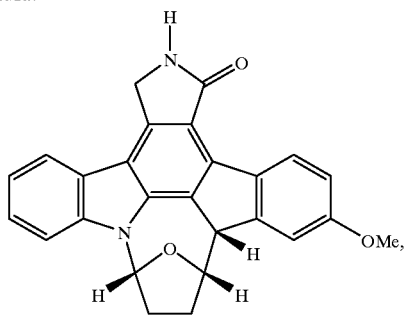
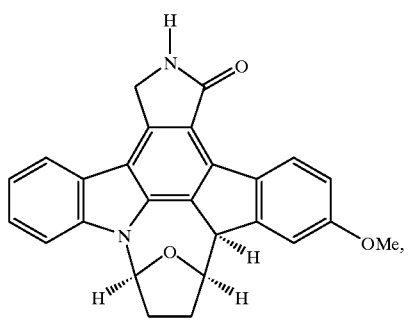
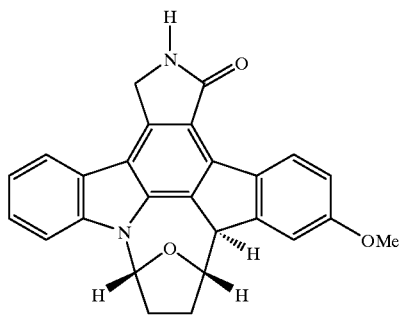
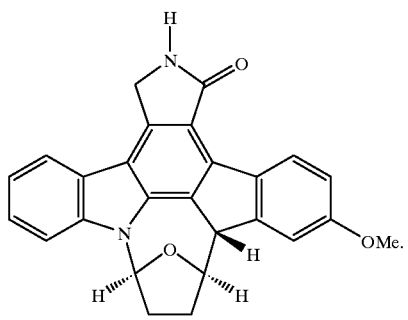

14. The compound of claim 12 having diastereomers of formula:
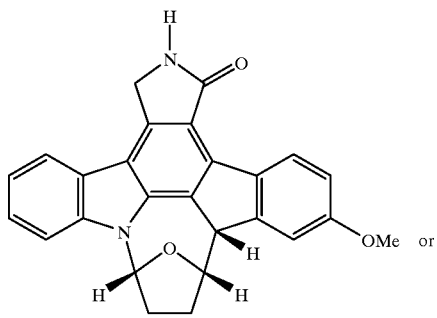 or 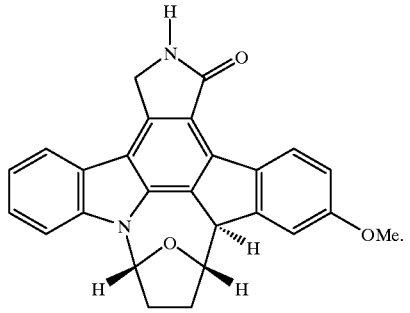

UNITED STATES PATENT AND TRADEMARK OFFICE
CERTIFICATE OF CORRECTION

PATENT NO. : 6,359,130 B1
DATED : March 19, 2002
INVENTOR(S) : Singh et al.

It is certified that error appears in the above-identified patent and that said Letters Patent is hereby corrected as shown below:

Title page,
Item [56], References Cited, OTHER PUBLICATIONS, "Grove et al.," reference, please delete "Diacylglycereols" and insert -- Diacylglycerols -- therefor.

Column 4,
Line 15, please delete "–$NR^{10}S(=O)_2R_9$" and insert -- –$NR^{10}S(=O)_2R^9$ -- therefor.

Column 18,
Line 59, please delete "trka" and insert -- trkA -- therefor.

Column 19,
Line 55, please delete "St. Lois" and insert -- St. Louis -- therefor.

Column 25,
Line 25, please delete "form" and insert -- from -- therefor.

Column 31,
Line 10, please delete "(s, 3H)" and insert -- (s, 1H) -- therefor.

Column 32,
Line 41, please delete "enatiomer" and insert -- enantiomer -- therefor.
Line 43, please delete "saparatly" and insert -- separately -- therefor.
Line 58, please delete "indivisual enetimers" and insert -- individual enantiomers -- therefor.

UNITED STATES PATENT AND TRADEMARK OFFICE
CERTIFICATE OF CORRECTION

PATENT NO.    : 6,359,130 B1
DATED         : March 19, 2002
INVENTOR(S)   : Singh et al.

It is certified that error appears in the above-identified patent and that said Letters Patent is hereby corrected as shown below:

Column 33,
Line 45, please delete "reisude" and insert -- residue -- therefor.

Signed and Sealed this

Twenty-first Day of June, 2005

JON W. DUDAS
*Director of the United States Patent and Trademark Office*